US012599902B2

(12) United States Patent
Jones et al.

(10) Patent No.: US 12,599,902 B2
(45) Date of Patent: Apr. 14, 2026

(54) AUTOMATED MICROSCOPIC CELL ANALYSIS

(71) Applicant: Medica Corporation, Bedford, MA (US)

(72) Inventors: Ronald Jones, Newton, NH (US); Adrian Gropper, Watertown, MA (US); Robert Hagopian, Belmont, MA (US); Charles Rogers, Halifax, MA (US); Thomas Vitella, Sandown, NH (US); Donald Barry, Jr., Groton, MA (US); Dirk Osterloh, Arlington, MA (US); Chen Yi, Boxborough, MA (US); Tyler Cote, Chelmsford, MA (US)

(73) Assignee: Medica Corporation, Bedford, MA (US)

( * ) Notice: Subject to any disclaimer, the term of this patent is extended or adjusted under 35 U.S.C. 154(b) by 616 days.

(21) Appl. No.: 17/972,469

(22) Filed: Oct. 24, 2022

(65) Prior Publication Data

US 2023/0294089 A1     Sep. 21, 2023

Related U.S. Application Data

(63) Continuation of application No. 15/017,498, filed on Feb. 5, 2016, now Pat. No. 11,478,789, which is a
(Continued)

(51) Int. Cl.
B01L 3/00         (2006.01)
G01N 1/10         (2006.01)
(Continued)

(52) U.S. Cl.
CPC ... B01L 3/502715 (2013.01); B01L 3/502738 (2013.01); G01N 15/1433 (2024.01);
(Continued)

(58) Field of Classification Search
CPC ......... B01L 3/502715; B01L 3/502738; B01L 2200/027; B01L 2200/0605;
(Continued)

(56) References Cited

U.S. PATENT DOCUMENTS 8,329,437 B1 * 12/2012 Ayliffe .............. G01N 15/1023
                                                   435/173.9
11,478,789 B2 * 10/2022 Jones ................... G06V 20/698
(Continued)

*Primary Examiner* — Brian J. Sines
(74) *Attorney, Agent, or Firm* — Kristofer E. Elbing

(57) ABSTRACT

This disclosure describes single-use test cartridges, cell analyzer apparatus, and methods for automatically performing microscopic cell analysis tasks, such as counting blood cells in biological samples. A small unmeasured quantity of a biological sample such as whole blood is placed in the disposable test cartridge which is then inserted into the cell analyzer. The analyzer isolates a precise volume of the biological sample, mixes it with self-contained reagents and transfers the entire volume to an imaging chamber. The geometry of the imaging chamber is chosen to maintain the uniformity of the mixture, and to prevent cells from crowding or clumping, when it is transferred into the imaging chamber. Images of essentially all of the cellular components within the imaging chamber are analyzed to obtain counts per unit volume. The devices, apparatus and methods described may be used to analyze a small quantity of whole blood to obtain counts per unit volume of red blood cells, white blood cells, including sub-groups of white cells, platelets and measurements related to these bodies.

16 Claims, 18 Drawing Sheets

Related U.S. Application Data continuation-in-part of application No. 14/947,971, filed on Nov. 20, 2015, now abandoned.

(60) Provisional application No. 62/138,359, filed on Mar. 25, 2015, provisional application No. 62/113,360, filed on Feb. 6, 2015, provisional application No. 62/084,760, filed on Nov. 26, 2014.

(51) Int. Cl.

| | |
|---|---|
| *G01N 1/30* | (2006.01) |
| *G01N 15/01* | (2024.01) |
| *G01N 15/10* | (2024.01) |
| *G01N 15/14* | (2024.01) |
| *G01N 15/1433* | (2024.01) |
| *G01N 15/1434* | (2024.01) |
| *G01N 21/05* | (2006.01) |
| *G01N 33/487* | (2006.01) |
| *G01N 33/49* | (2006.01) |
| *G01N 33/50* | (2006.01) |
| *G01N 33/80* | (2006.01) |
| *G01N 35/00* | (2006.01) |
| *G06V 20/69* | (2022.01) |

(52) U.S. Cl.
CPC ..... *G01N 15/1434* (2013.01); *G01N 15/1484* (2013.01); *G01N 33/487* (2013.01); *G01N 33/49* (2013.01); *G01N 33/4915* (2013.01); *G01N 33/5094* (2013.01); *G01N 33/80* (2013.01); *G06V 20/693* (2022.01); *G06V 20/698* (2022.01); *B01L 2200/027* (2013.01); *B01L 2200/0605* (2013.01); *B01L 2200/0647* (2013.01); *B01L 2200/16* (2013.01); *B01L 2300/0627* (2013.01); *B01L 2400/0633* (2013.01); *B01L 2400/0644* (2013.01); *G01N 1/10* (2013.01); *G01N 1/30* (2013.01); *G01N 15/01* (2024.01); *G01N 2015/016* (2024.01); *G01N 2015/018* (2024.01); *G01N 2015/1006* (2013.01); *G01N 2015/1486* (2013.01); *G01N 21/05* (2013.01); *G01N 2035/00148* (2013.01); *Y10T 436/101666* (2015.01)

(58) Field of Classification Search
CPC ......... B01L 2200/0647; B01L 2200/16; B01L 2300/0627; B01L 2400/0633; B01L 2400/0644; G01N 15/1433; G01N 15/1434; G01N 15/1484; G01N 33/487; G01N 33/49; G01N 33/4915; G01N 33/5094; G01N 33/80; G01N 1/10; G01N 1/30; G01N 15/01; G01N 21/05; G01N 2015/016; G01N 2015/018; G01N 2015/1006; G01N 2015/1486; G01N 2035/00148; G06V 20/693; G06V 20/698; Y10T 436/101666
See application file for complete search history.

(56) References Cited

U.S. PATENT DOCUMENTS

| | | | | |
|---|---|---|---|---|
| 2002/0028471 A1* | 3/2002 | Oberhardt | .......... | G01N 15/1433 |
| | | | | 382/133 |
| 2010/0050749 A1* | 3/2010 | Yuan | ................. | B01L 3/502715 |
| | | | | 435/293.1 |
| 2011/0256026 A1* | 10/2011 | Kim | ...................... | B01L 3/5027 |
| | | | | 422/68.1 |
| 2012/0291538 A1* | 11/2012 | Ludowise | ......... | B01L 3/502738 |
| | | | | 73/149 |
| 2013/0167945 A1* | 7/2013 | Mehta | .................... | F16K 17/40 |
| | | | | 137/68.19 |
| 2016/0091483 A1* | 3/2016 | McCluskey | ............. | B01L 3/567 |
| | | | | 422/501 |
| 2017/0328924 A1* | 11/2017 | Jones | .................... | G01N 1/312 |

* cited by examiner

| Description | Bright-field | Fluorescent |
|---|---|---|
| Lymphocyte | | |
| Monocyte | | |
| Neutrophil | | |
| Eosinophil | | |
| Basophil | | |
| Nucleated Red Blood Cell | | |

AUTOMATED MICROSCOPIC CELL ANALYSIS

CROSS-REFERENCE TO RELATED APPLICATIONS

This application is a continuation of U.S. application Ser. No. 15/017,498, filed Feb. 5, 2016, which claims priority to U.S. application Ser. No. 14/947,971, filed Nov. 20, 2015, and to US provisional applications Nos. 62/138,359, filed Mar. 25, 2015, 62/084,760, filed Nov. 26, 2014, and 62/113, 360 filed Feb. 6, 2015, which are all herein incorporated by reference.

FIELD OF THE INVENTION

This invention pertains to analyzers and methods for automatically performing microscopic cell analysis tasks, such as counting blood cells in biological samples. More specifically, the present disclosure relates to single use devices, apparatus and methods used to count red blood cells, white blood cells and platelets, and measurements related to these bodies.

BACKGROUND OF THE INVENTION

There are a variety of methods for enumerating particles, such as cells in a biological sample. Determining the number of cells per unit volume in a sample provides the physician important diagnostic information. The most elementary method of counting cells consists of introducing a diluted biological sample into a hemocytometer and examining it with a microscope. A hemocytometer is a device with an optically clear chamber having a known depth, typically 100 microns, and ruled markings to define a unit volume, typically 0.01 μL. A uniform mixture of diluted whole blood, for example, may be introduced into the hemocytometer by capillary action to form a monolayer. Using a microscope to visualize the diluted sample, cells of different types can be counted manually in a limited number of marked areas. Counts are aggregated to compute the number of cells per unit volume. This manual method is time consuming, tedious, and requires a skilled technician to operate the microscope and to recognize the various types of cells, and is prone to error. Its accuracy is limited by the number of cells counted and the homogeneity of the monolayer formed by introduction of the diluted sample.

Consequently, automated methods, such as impedancemetry (Coulter principle U.S. Pat. No. 2,656,508) and flow cytometry, have been developed for rapid counting, sizing, and classification of a relatively large number of cells for diagnostic tests such as the Complete Blood Count (CBC) or CBC with a five part differential. These automated methods also have shortcomings. The analyzers are relatively large and expensive and require skilled operators for their use and maintenance. Such analyzers are typically available only in centralized laboratories. Blood samples are collected in special containers having an anticoagulant to keep the blood from clotting while being transported to the lab. This process adds costs and risk of erroneous results from transport, handling, labeling and transcription, as well as a time delay in obtaining the results.

The CBC generally includes measures of white blood cells (leukocytes) per unit volume (WBC), red blood cells (erythrocytes) per unit volume (RBC), platelets (thrombocytes) per unit volume (PLT), hematocrit (HCT) or packed cell volume (PCV), hemoglobin (HGB), and measurements related to red cells including mean corpuscular volume (MCV), mean corpuscular hemoglobin (MCH), mean corpuscular hemoglobin content (MCHC), and red cell distribution width (RDW). A diagnostic test referred to as a "CBC with differential", also known as a "CBC with five part diff", will also include Neutrophil granulocytes (NEU), Lymphocytes (LYM), Monocytes (MON), Eosinophil granulocytes (EO) and Basophil granulocytes (BASO) per unit volume or as a percentage of the white blood cells (WBC). The CBC with differential also may include counts of Immature Cells (IC), nucleated Red Blood Cells (nRBC), and Reticulocytes (RETIC) per unit volume of the blood sample.

The CBC provides a panel of blood cell measurements that can be used to diagnose a wide variety of abnormal conditions, such as anemia or infection, or to monitor a patient's treatment, such as chemotherapy. Because of its usefulness, the CBC analysis is one of the most commonly performed diagnostic tests in medicine, but patients typically wait a day or more for results. If microscopic cell analysis could be performed in a portable, easy-to-use, analyzer close to the patient, results could have a more immediate impact in improving patient care. A simple system able to provide the CBC in the physician's office, or at bedside, or in the Critical Care Unit (CCU) or Intensive Care Unit (ICU), within a few minutes and using a drop of blood from a finger-stick, could have enormous impact on the delivery and affordability of health care.

Recent patent documents have described simpler devices than centralized lab hematology analyzers for performing cell analysis of blood samples. In U.S. Pat. No. 7,771,658, issued to Larsen, the applicant, provides technology for performing a flow-cell analysis of blood cells in a single use disposable cartridge. Larsen describes means for taking an exact amount of blood sample, diluting the amount of blood with a precise volume of diluent, and mixing the blood with the diluent to obtain a homogeneous solution. Larsen utilizes a single use cartridge to flow a measured amount of the mixture of sample and diluent through an orifice at a rate of several thousand particles per second, and counts, sizes, and classifies the particles for analysis in accordance with the Coulter principle. Because Larsen's disclosure is directed to the analysis of a small sample of whole blood, errors in metering various volumes or in the mixing or sampling steps can significantly impact the accuracy of the results.

PCT Patent Number WO 2014099629 issued to Ozcan et al. describes a system for analyzing a blood sample with a mobile electronic device having a camera. The sample preparation process for each test requires accurate measurement of 10 μL of whole blood to be mixed with 85 μL phosphate buffered saline and 5 μL of nucleic acid stain. Ten (10) μL of this diluted mixed sample are then loaded into a cell counting chamber with precise channel height of 100 μm and are imaged by a digital camera. A separate cell counting chamber is needed for analysis of red cells, white cells, and hemoglobin, and each test should be performed separately. Accuracy of the final result is not only dependent on the accurate measurements of the various sample preparation steps, including the precise metering of the sample and diluent, but also on the precise fabrication of the counting chambers. Maintaining uniformity and consistency of the 100 μm dimension of the channel height in a disposable cartridge is difficult to achieve in a low cost device.

U.S. Pat. No. 8,837,803 to Wang et al. describes a method for determining cell volume of red blood cells, which seeks to avoid the errors associated with diluting, mixing, and sampling, by analyzing a sample of substantially undiluted whole blood. In theory this approach has appeal, but the handling of undiluted whole blood is challenging. The cells are so numerous (for example 5,000,000 red cells in 1 µL) that their distribution can be impacted by contact with the surfaces of a disposable cartridge. Additionally, in order to image cells in this overcrowded environment, the imaging chamber should have a depth of only a few microns to prevent the overlapping of cells, and it should be fabricated accurately, because it determines the volume of the blood sample being analyzed.

Therefore a compact, accurate method of performing microscopic cell analysis using digital camera imaging of a diluted sample, which does not require accurate measurement of the diluent volume, or require accurate or precise dimensions of an imaging chamber, is highly desirable.

SUMMARY OF THE INVENTION

An objective of the present invention is to provide an apparatus that can provide counts of cells or other particles of a biological sample per unit volume without requiring an operator having specialized knowledge or specialized skills. Another objective of the present invention is to provide an easy-to-use apparatus that can perform all of the measurements of the CBC in a few minutes. Another objective of the present invention is to provide a method for determining the concentration of particles in a diluted biological sample that does not require accurate measurement of a volume of diluent or reagent mixed with the sample. Another objective of the present invention is to provide ready-to-use reagents for use in performing the microscopic analysis of a biological sample that do not require preparation, mixing or measurement by the user. Another object of the invention is to create a substantially homogenous monolayer of cells of a diluted sample in a single use disposable device and to perform a CBC analysis in a few minutes. Another objective is to provide a sample collection device that can easily be operated by a user to obtain a biological sample for analysis. Yet another objective is to provide all of the fluidic components of an apparatus to perform a CBC in a single-use device, so as to prevent cross contamination between samples and to avoid the need for cleaning and washing of fluidic components. Another objective of the present invention is to provide internal monitoring of the critical process steps of counting cells, so that a potentially erroneous result can be flagged. Still another objective is to provide a method of performing the CBC immediately after collecting the sample, and to eliminate transport of the sample to a laboratory or storage of the sample. Some or all of these and/or other objectives or advantages may be accomplished by embodiments of the invention as provided for in the appended claims.

The disclosure provides improved methods, systems, and devices for performing counts and measurements of particles in a biological sample. Aspects of the disclosure are directed to determining the concentration of one or more types of particles and providing the result as the number of such particles per unit volume of the biological sample in a few minutes. The particles may be any mass suspended in a liquid that can be recognized by optical inspection using an automated microscope and image analysis techniques well known in the art. Examples of particles include, but are not limited to, blood cells, sperm, bacteria, spores, and inorganic particles.

While embodiments of the present invention can be used in many applications to count particles suspended in a liquid, the present disclosure will demonstrate benefits of the invention in performing the Complete Blood Count (CBC) or CBC with differential on human blood samples as defined above. The present disclosure describes a single-use test cartridge for use with an apparatus that includes an automated microscope for analyzing cells in a biological sample. The test cartridge is used to collect a biological sample. For example the user can prick the finger of a patient and obtain a whole blood sample and collect the resulting drop of blood in the test cartridge. The user can accomplish this by holding the test cartridge beneath the hanging drop from the patient's finger and then bringing it closer until the drop contacts an input port or sample cup on the test cartridge. In an alternate embodiment, the user may collect a blood sample intravenously and transfer it to the test cartridge using a capillary tube or plastic bulb pipette. In one example the single-use test cartridge includes an input port adapted to accept a variety of sources of biological samples including a direct sample, capillary tube, or transfer pipette. In another example, the test cartridge could draw a sample into it by capillary action. The test cartridge may also include a closure that the user applies to cover the input port after the sample has been collected into the test cartridge. The closure may be part of the test cartridge or a separate device. The user may apply the closure manually or the apparatus may automatically move the closure to cover the input port when the test cartridge is docked to the apparatus. The closure provides a physical barrier to avoid subsequent contact with any excess sample on the surface of the test cartridge. The closure has a vent to provide an air path to the input port to allow the liquid sample to move within the test cartridge, as will be described below.

Within the test cartridge, the input port is connected by an input channel to a metering chamber capable of precisely separating a small volume of the sample from the unmeasured sample. As an example, the collected sample volume may be 5-20 µL of which the metering chamber separates out or isolates 0.1-5 µL for measurement. If a finger stick sample is utilized, a sample volume less than 10 µL will minimize the risk of hemolysis and the risk of dilution by interstitial fluids. The metering chamber can be a section of a fluid channel, a cavity, or a pass-through conduit within a valve, or another volumetric shape that can be reproducibly fabricated to contain a predetermined volume of the biological sample in the range of 0.1 to 5 µL. Injection molding, compression molding, etching or other processes known to those skilled in the making of lab-on-a-chip or microfluidic devices can be utilized to manufacture the metering chamber.

In one example, the metering chamber is combined with a rotary valve structure by molding a pass-through conduit in the cylindrical stem of the rotary valve. As an example a pass-through conduit having a cylindrical cross section with 0.5 mm diameter and a length of 5 mm, has an internal volume of approximately 1 µL. The pass-through conduit is initially filled with the biological sample by providing a fluid communication path between the input port and input channel, the pass-through conduit, and a vacuum channel. A vacuum applied to the vacuum channel pulls the sample into the pass-through conduit. Alternatively the biological sample can be pulled into the pass-through conduit by capillary attraction. Once the biological sample has completely filled the pass-through conduit, the cylindrical stem of the rotary valve is rotated until the pass-through conduit is no longer connected to the input channel or the vacuum channel, thus separating or isolating the sample volume contained in the pass-through conduit. Alternatively, a rotary face seal valve, a slide valve or a fixed geometry in the test cartridge could be used to isolate a small volume of the sample.

Further, elements of the test cartridge include a prepackaged liquid reagent or alternatively, a chamber for storing a liquid reagent, together with a mixing chamber, an imaging chamber, and fluid channels through which the sample and liquid reagent may be moved. In one example, after the biological sample has filled the pass-through conduit, the rotary valve is positioned so that the pass-through conduit is placed in fluid communication with both a liquid reagent and the mixing chamber. Empirical studies have determined that a volume of diluent or liquid reagent or stain (referred to here as "diluent/reagent") that is in excess of 3-times the volume of the pass-through conduit is sufficient to wash out the entire isolated sample. In one example, the diluent/reagent is a combination of diluent and stain and is supplied in a volume to provide a dilution ratio of about 40:1. Therefore forty times the volume of the metering chamber can be used to push the isolated sample out of the pass-through conduit and into the mixing chamber, where the sample is uniformly mixed with the diluent/reagent, and then transferred into the imaging chamber.

The single use test cartridge contains an imaging chamber, through which an automated microscope can acquire images of cells in the mixture of diluent/reagent and sample. In one embodiment of the present invention, the isolated sample is diluted with a known volume of diluent/reagent, whereby the dilution ratio is established. The volume of the diluent/reagent may be determined by measuring it, for example, by monitoring its flow in a fluid channel of known dimensions with a camera or other fluid sensor such as optical reflective/transmittive or ultrasonic, or by temporarily metering it into a known volume chamber and then using only that known volume for sample dilution. According to this embodiment, the cells in a known volume of the diluted sample are counted, and because the dilution ratio is known, the cell counts per unit volume of the blood sample can be determined. The volume of the diluted sample can be known by filling an imaging chamber of known volume with the diluted sample. The volume of the imaging chamber may be known by using highly reproducible manufacturing processes, or by measuring each test cartridge at time of manufacture and encoding sizing parameters in the package labeling. Alternatively, a measured amount of the diluted sample can be transferred into an imaging chamber of unknown volume and counting all the cells in the chamber. A measured amount of the diluted sample can be determined by monitoring its flow from the mixing chamber into a fluid channel of known dimensions by a camera, and isolating a segment. The segment, in turn, is moved into the imaging chamber.

In a preferred embodiment, the entire isolated sample is transferred to the mixing chamber and then to the imaging chamber. According to this embodiment, neither the dilution ratio nor the volume of the diluent needs to be known. The size of the imaging chamber is chosen to ensure that the entire volume of the isolated sample and the diluent/reagent can be contained within the imaging chamber, but the exact dimensions or volume of the chamber do not need to be known. The depth of the imaging chamber should be small enough to prevent the cells from overlapping at the chosen dilution ratio when the cells settle to the bottom. This depth is preferably between about 10 μm and 200 μm. In one embodiment, the depth of the imaging chamber is 100 μm and the ratio of the diluent/reagent to the isolated sample is 40 to 1. The width of the imaging chamber is chosen to provide uniform filling by the different cell sizes and smooth flow without forming voids or crowding of cells. The length of the imaging chamber is calculated based on the depth and width parameters to provide the volume needed to accommodate the entire isolated sample at the chosen dilution ratio, and to provide a margin of safety. The shape of the imaging chamber may further be chosen to match the field of view of the digital camera or to facilitate capture of multiple images or to maintain a uniform distribution of cells We have found that if the shape of the imaging chamber is square or rectangular having a ratio of length to width of 2:1, the cells will not uniformly fill the imaging chamber. If the mixture of sample and diluent/reagent is uniform when it enters the imaging chamber, the cells will tend to bunch and crowd, particularly near the sides or edges, and when they settle, the layer on the bottom of the imaging chamber will not be homogenous. It is important to obtain a substantially homogenous monolayer of cells in the imaging chamber, as this facilitates the counting of all the cells. We have found that if the width and depth of the imaging chamber are small compared to the length, the cells remain more uniformly distributed. Desirably, the length-to-width ratio of the imaging chamber is greater than 10:1. In various embodiments of the present invention, the shape of an imaging chamber may be serpentine, helical, or castellated according to the form factor of the test cartridge. In all of these cases the width and depth are small compared to the length so that the cells due not aggregate on the sides or corners of the imaging chamber, and the layer of cells settling to the bottom of the imaging chamber is substantially homogenous. Those skilled in the art will recognize that other geometries for the imaging chamber, which maintain the distribution of cells when the mixed solution of sample and diluent/reagent is transferred into the imaging chamber may also be utilized.

The design goal of any imaging chamber is to contain all the cells from the original metered chamber and the diluent/reagent in a uniform manner and without significant cell overlap when the cells settle to the bottom of the imaging chamber. The dilution ratio combined with the depth of the imaging chamber can be chosen to minimize the overlapping. As an illustrative example, an imaging chamber may have a width between 0.5 mm and 2.5 mm, a depth from 10 to 200 μm, and the dilution ratio may be from 10:1 to 100:1.

Materials, which contact the cells outside of the imaging chamber, may be chosen to have surface properties to minimize cell adherence. Liquid reagents, which may include a surfactant or cell sphering agent to facilitate cell analysis, may also advantageously minimize red cells being lost during transfer or being overlapped in the imaging chamber. The volume of liquid reagent and the flow velocity may also be chosen to improve the likelihood of transferring every cell from the metering or mixing chamber to the imaging chamber and insuring that the distribution of the cells remains uniform. Yeh-Chan Ahn describes the complex convective diffusion phenomena that is created in a serpentine microchannel which has a varying curvature (See *Investigation of laminar dispersion with optical coherence tomography and optical Doppler tomography*, Yeh-Chan Ahn, Woonggyu Jung, Jun Zhang, and Zhongping Chen, OPTICS EXPRESS 8164, Vol. 13, No. 20, 3 Oct. 2005). Particles, or in our case, cells which are in suspension and moving through such a microchannel tend to segregate according to their size, density, channel shape and flow velocity. Secondary flow from the serpentine geometry can create vortices as the channel curves causing the cells to be re-mixed into the center of the flow at certain fill velocities. This re-mixing helps maintain a near uniform distribution of the cells as the fluid fills the microchannel. In one embodiment, we have found that a serpentine path that is 1.25 mm wide with turning inside diameter of 1.25 mm and an outside diameter of 2.5 mm, a depth of 0.125 mm, a length of 500 mm, and an effective fill speed of about 2 μL/s insures that the flow of cells remains uniform.

It should be noted that the time to count every cell is directly related to the volume of the metered chamber, and that this creates a trade-off in overall performance. Manufacturing highly reproducible metering chambers is challenging for very small volumes. Therefore while it may be easier and more reproducible to manufacture a metering chamber with a 5 μL volume than one with a 1 μL volume, the 5 uL volume of sample would potentially take five times longer to analyze. Embodiments of the present invention can provide a solution to this dilemma. By ensuring that the sample and diluent/reagent are well mixed and that a proper dilution ratio is chosen, and by utilizing a serpentine shaped imaging chamber where the length is large compared to the width and depth, the pattern of cells across the imaging chamber is relatively uniform and highly reproducible. Under these conditions, the layer of cells settling to the bottom of the imaging chamber will be a substantially homogenous monolayer. As a result, instead of imaging the entire layer and counting every cell, one can take representative images or frames that are statistically derived to accurately account for every cell. Thus, within the allowable error for the final result(s), every cell is included in the analysis, whether by actual image or by statistical representation. As an illustrative example, the camera may take up to 20,000 images at 20× in order to scan the entire imaging chamber. Alternatively, every tenth frame could be taken to obtain a statistical representation. Another option would be to divide the imaging chamber into segments and count the cells in every other segment or every third segment and so on. Another alternative to decrease the imaging time would be to scan the entire imaging chamber at 10×/0.25NA or 4×/0.1NA to obtain the total WBC and RBC total counts, and then take images at higher power (20×0.4NA or higher) to obtain the higher-resolution detail needed for counting platelets, reticulocytes, and performing the WBC differential.

Embodiments of the present invention can achieve accurate results that are not dependent on many factors that have impacted the accuracy of results in the prior art. For example, the volume of the diluent/reagent and the dilution ratio do not impact the results, so long as all the cells from the metered volume are transferred to the imaging chamber and presented for analysis. Similarly the representativeness of a selected sub-volume of the mixture of sample and reagent, and the homogeneity of the sub-volume, which directly affect the accuracy of results by prior art methods, need have no impact on embodiments the present invention. Most importantly, the depth and uniformity of the imaging chamber, which has been difficult or expensive to control in other prior art efforts, need not impact the accuracy of results according to embodiments of the present invention.

The present disclosure further describes a cell analyzer that is small and easy to use. The cell analyzer accepts the test cartridge and carries out all the steps of the cell analysis without further input from the user. In one embodiment, the test cartridge contains all diluents and reagents needed to perform a CBC analysis of the patient sample placed in it. In this embodiment, the cell analyzer has fluid handling components including positive and negative pressure sources that interface with the test cartridge when it is placed into the analyzer. One or more connections are made between the analyzer and the cartridge to place these pressure sources into fluid communication with channels in the cartridge to provide a motive force to move liquids within the cartridge. The cell analyzer also has a mechanical valve driver for operating a valve in the test cartridge for controlling the movements of fluids in the test cartridge. When the test cartridge is placed in the analyzer, the mechanical valve driver is connected to a valve indexer to provide means for operating the valve in the test cartridge. The cell analyzer includes a mechanism for release of the diluent/reagent that are stored on board the test cartridge. The cell analyzer further includes fluid control logic to automatically control movement of the fluids in the test cartridge by activating the positive and negative pressure or displacement sources and operating the mechanical valve driver according to pre-programmed sequences. The cell analyzer may include a process monitoring camera positioned to acquire digital images of the movement of fluids in the cartridge. Information from the process monitoring camera can be used to provide feedback for the fluid control logic or for monitoring critical steps.

The present disclosure also provides devices and methods for managing and/or monitoring the sample collection and preparation process to ensure accurate results. In applications where the present invention is used to perform a CBC analysis, if too much time lapses between obtaining the blood sample and completing sample dilution and staining within the test cartridge, the blood may clot or the cells may settle resulting in erroneous results. In one embodiment of the present invention that mitigates this risk, the test cartridge is placed on the analyzer in a slide-out tray which initiates process monitoring within the analyzer. The blood sample is added to the cartridge by dispensing a free-hanging drop, or by using a capillary tube that is inserted into the test cartridge. Immediately after the sample has been added to the cartridge, the user presses "Run Sample" to initiate the test sequence. Because the cartridge is controlled by the analyzer, the time to collect the sample is known and can be short enough to avoid the need for anticoagulant coating or mixing the blood sample.

In an alternate embodiment that allows the sample to be collected several minutes before processing, an anticoagulant, such as K2 or K3 EDTA, is provided. This may be achieved by coating the sample input cup with anticoagulant, by use of a capillary tube coated with anticoagulant for a finger-stick sample, or by sampling from an evacuated blood collection tube such as a Becton Dickenson Vacutainer® containing anticoagulant. To manage cell settling, the test cartridge according to this embodiment has a timing indicator which is initiated when the input port is opened or the blood sample is introduced. The timing indicator can be a color-changing chemical reaction, a time delayed thermal reaction, an analog or digital timer, or other means known in the art. When the user loads the test cartridge into the analyzer, the timing indicator is read and if needed, the sample is mixed before proceeding. If too much time has lapsed the sample can be rejected to avoid producing erroneous results.

In yet another embodiment that facilitates remote sample collection, the test cartridge is docked to a carrier system. The carrier system is a handheld or portable device used to facilitate a portion, or all, of the sample preparation steps. After blood is added to the test cartridge using any of the above mentioned methods, the carrier system according to this embodiment draws the blood into the cartridge, meters the sample, performs quality checks, and completes the sample preparation to present the cells for image analysis. The carrier system would then either eject the test cartridge for the user to transfer to the imaging analyzer, or the carrier system could be docked to the imaging analyzer for an automated handoff. In this embodiment anticoagulant coatings are not needed and there is no risk of cell settling because the critical steps are initiated as soon as the sample is placed in the test cartridge.

Combinations of the workflow devices and methods are also contemplated in the present disclosure. By way of example, a simple carrier system could incorporate a digital timer and a mechanism able to meter the sample, but not perform quality checks or full sample preparation. These additional steps would be done by the cell analyzer.

The cell analyzer contains an automated microscope including an objective lens, focusing mechanism, bright-field and fluorescent light sources, filters, a dichroic mirror and a digital camera. In some embodiments, the cell analyzer may further include an illumination source and photometric detector for measuring light transmission at one or multiple wavelengths for measuring the concentration of an analyte in the sample. For example, the test cartridge can include a photometric chamber which is in fluid communication with the input port by means of a fluidic channel, and through which the sample can be transferred for photometric analysis, such as a hemoglobin measurement.

By way of example, to measure hemoglobin, the cell analyzer may have an illumination source consisting of two light emitting diodes (LEDs) providing excitation at wavelengths of 502 nm and 880 nm. The light path for the LEDs and a photometric detector are approximately 0.030" diameter. The 502 nm LED may be selected for absorbance measurement because of an isobestic point of oxyhemoglobin (O2Hb) and deoxyhemoglobin (RHb). Also at 502 nm, the slope of the O2Hb and RHb curves are very low, resulting in minimal variation with varying oxygen saturation (sO2) levels. Furthermore, the carboxyhemoglobin (COHb) curve is also close to this isobestic point, resulting in very little effect from COHb. An 880 nm LED can measure the background scatter effects caused by RBCs, WBCs, lipids, etc. This is particularly important when taking measurements on whole blood. This measurement may also be performed on lysed blood, with or without a reagent for converting the hemoglobin to a single form, such as reduced hemoglobin, methemoglobin, azidemethemoglobin or cyanomethemogloin. In the case of a conversion to a single form of hemoglobin, a different peak wavelength for absorption measurement may be used, such as 540 nm or 555 nm.

Disclosed and contemplated aspects also include an example of a test cartridge that is not preloaded with reagents, and instead, is coupled to a reagent supply module contained on board the cell analyzer. The user loads the reagent supply module into the cell analyzer where it is utilized for multiple test cartridges. When the reagent supply module is exhausted or expires, the cell analyzer alerts the user and will not perform additional tests until the reagent supply module is exchanged. The reagent supply module includes a cradle for receiving the test cartridge, a vessel for holding a liquid diluent/reagent, a diluent delivery pump in fluid communication with the vessel, and a diluent/reagent output port constructed to interface with the test cartridge when the cartridge is in the cradle. In one example the size of the vessel is of sufficient capacity to provide diluent/reagents to dilute several samples (50-100) with a reagent to sample ratio of 10:1 to about 250:1. The diluent/reagent supply module may include a self-priming mechanism for priming the liquid reagent and eliminating air bubbles. The reagent supply module may further include a chamber for collecting waste diluent/reagent from the priming process.

In another embodiment contemplated in the present disclosure, a small measured volume of whole blood may be mixed manually with an unknown amount of diluent/reagent in a sample preparation device. For instance, the known volume of sample and unknown diluent/reagent may be put into a sample tube and gently rocked back and forth a few times. The entire mixed volume is then transferred by using a transfer pipette or similar device to a test cartridge having an imaging chamber. According to embodiments of the present invention, if all of the cells in the imaging chamber are counted (either directly or by statistical sampling), then the concentration of cells per unit volume can be determined, without one needing to know the volume of the diluent/reagent, the dilution ratio, or the volume of the mixed sample in the imaging chamber, or the volume of the imaging chamber occupied by the mixture.

Diluent/reagents that are preloaded in the test cartridge, or are provided in a separate sample preparation device, or by a supply module are in a ready-to-use format. For a CBC analysis, the reagents may include a membrane-permeable dye, such as Acridine Orange to differentially stain the DNA and RNA of cells in whole blood. Other stains known to those skilled in the art, such as cyanine dyes, can also be used to stain the blood cells. In an alternative arrangement, the stain may be provided in a dry reagent form together with a diluent that is mixed with the dry reagent as needed. Multiple stains can be included in a combination reagent. In one embodiment, the reagents may include an antibody conjugated to a detectable label that targets specific cells or specific antigens associated with cells. The detectable label may be a dye, a fluorescent dye, quantum dot, colloidal metal such as gold, silver, or platinum or other detectable constructs known in the art. The detectable label can also be used to detect a cell-specific antibody, such as CD3, CD4, CD14, CD16, CD19, CD34, CD45, CD56, or any other of the enumerated Cluster of Differentiation markers. The detectable label can also be used to detect bacterial or parasitic pathogens, platelets, recirculating tumor cells, leukemic cells, stem cells or any combination of these.

In other embodiments the liquid reagent may contain a surfactant such as polysorbate or sodium dodecyl sulfate (SDS), an anticoagulant such as EDTA, and/or a sphering agent such a zwitterionic detergent to provide isovolumetric reshaping of the red blood cells to facilitate cell size measurement and computation of the mean corpuscular volume (MCV).

Systems according to the invention can exhibit better quantitative accuracy than manual microscope analyses using a manual hemocytomer or similar device, which tend to be limited by variability in sample preparation and limited counting statistics. In embodiments of the present invention, sample preparation is improved by removing critical operator fluid handling steps and by automation of all dilution steps. Because every cell and platelet is counted in the entire metered volume of sample, any error in the sample dilution is irrelevant.

Systems according to the invention can also save time that would otherwise be allocated to manual hemocytometer slide preparation, setup time, and microscope focusing, which can limit the number of blood samples that can be analyzed. Automation can greatly increase the rate of image acquisition and analysis, allowing for more cells to be analyzed and counted. This can improve the counting statistics and overall precision of the system.

Systems according to the invention can also extend the capabilities of cell counting methods by enabling CBC point-of-care testing, i.e. near patient testing, to permit immediate clinical decisions to be made. Personnel having a relatively low skill level can operate the systems. The analyzers can be engineered to be inexpensively manufactured and easily serviced, allowing them to be more readily deployed at point-of-care sites, such as at the patient's bedside, in physician's offices, and at emergency sites.

BRIEF DESCRIPTION OF THE DRAWINGS

In the drawings, like reference characters generally refer to the same parts throughout the different views. The drawings are not necessarily to scale, emphasis instead being placed upon illustrating the principles of the invention. In the following description, various embodiments of the present invention are described with reference to the following drawings, in which.

DETAILED DESCRIPTION

Figure 1:
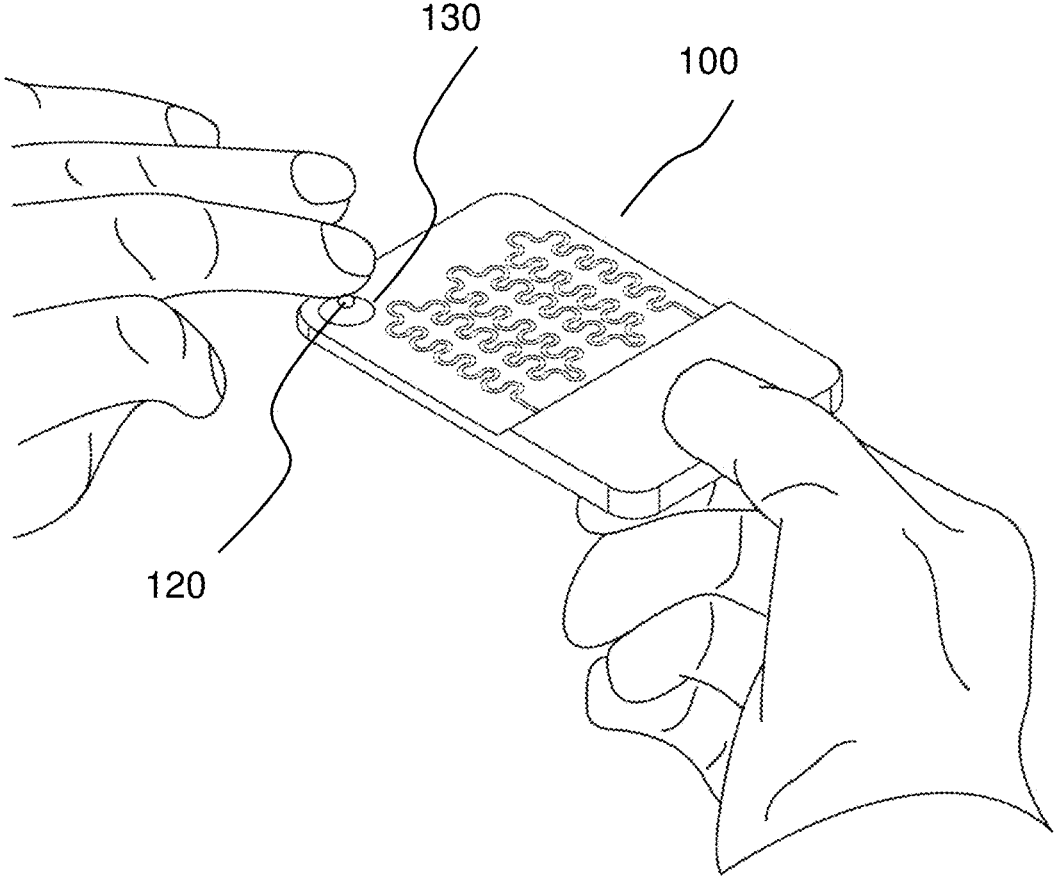
FIG. 1 is a perspective view of an illustrative test cartridge being positioned to collect a drop of blood from a patient's finger.

FIG. 1 illustrates test cartridge 100 being positioned to collect a drop of blood 120 from a patient's finger. The test cartridge is held beneath the hanging drop 120, so that it contacts the input port 130 of the test cartridge 100. The input port 130 comprises a recessed area or opening that may be coated with an anticoagulant and have surface treatment or features such as small columns to increase surface retention to collect and hold the blood sample. In an alternate embodiment, the blood sample 120 may be collected intravenously and introduced to input port 130 by a transfer pipette or capillary tube. The transfer pipette or capillary may contain an anticoagulant coating according to the desired workflow. The volume of blood or other biological sample placed in input port 130 is sufficient to visually fill the recessed sample area, but is unmeasured.

Figure 2A:
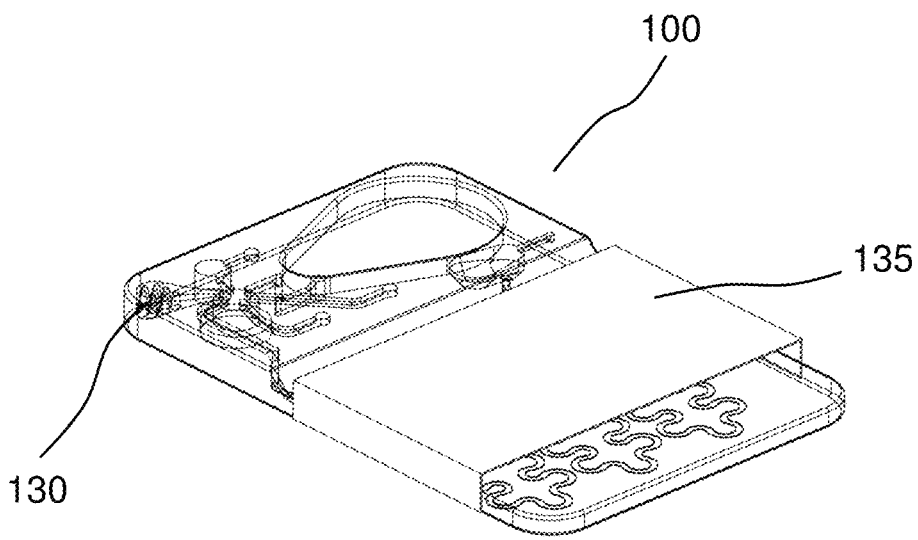
FIG. 2A is a perspective view of an illustrative test cartridge with a cover shown in the open position to receive a biological sample.
Figure 2B:
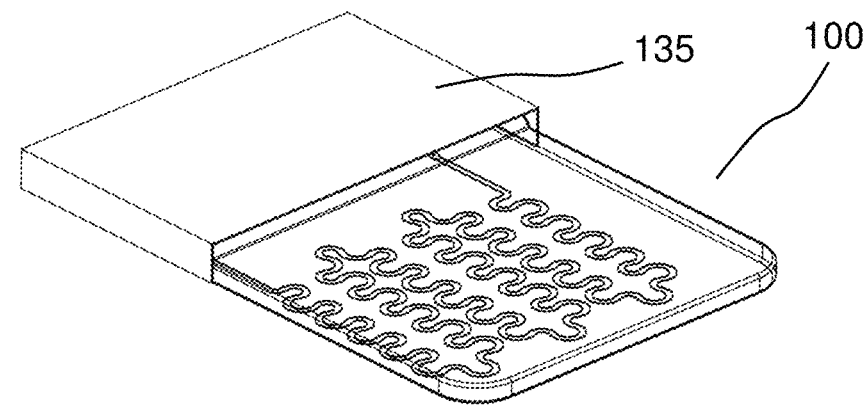
FIG. 2B is a perspective view of the test cartridge shown in FIG. 2A with the cover shown in the closed position ready for analysis.
Figure 3:
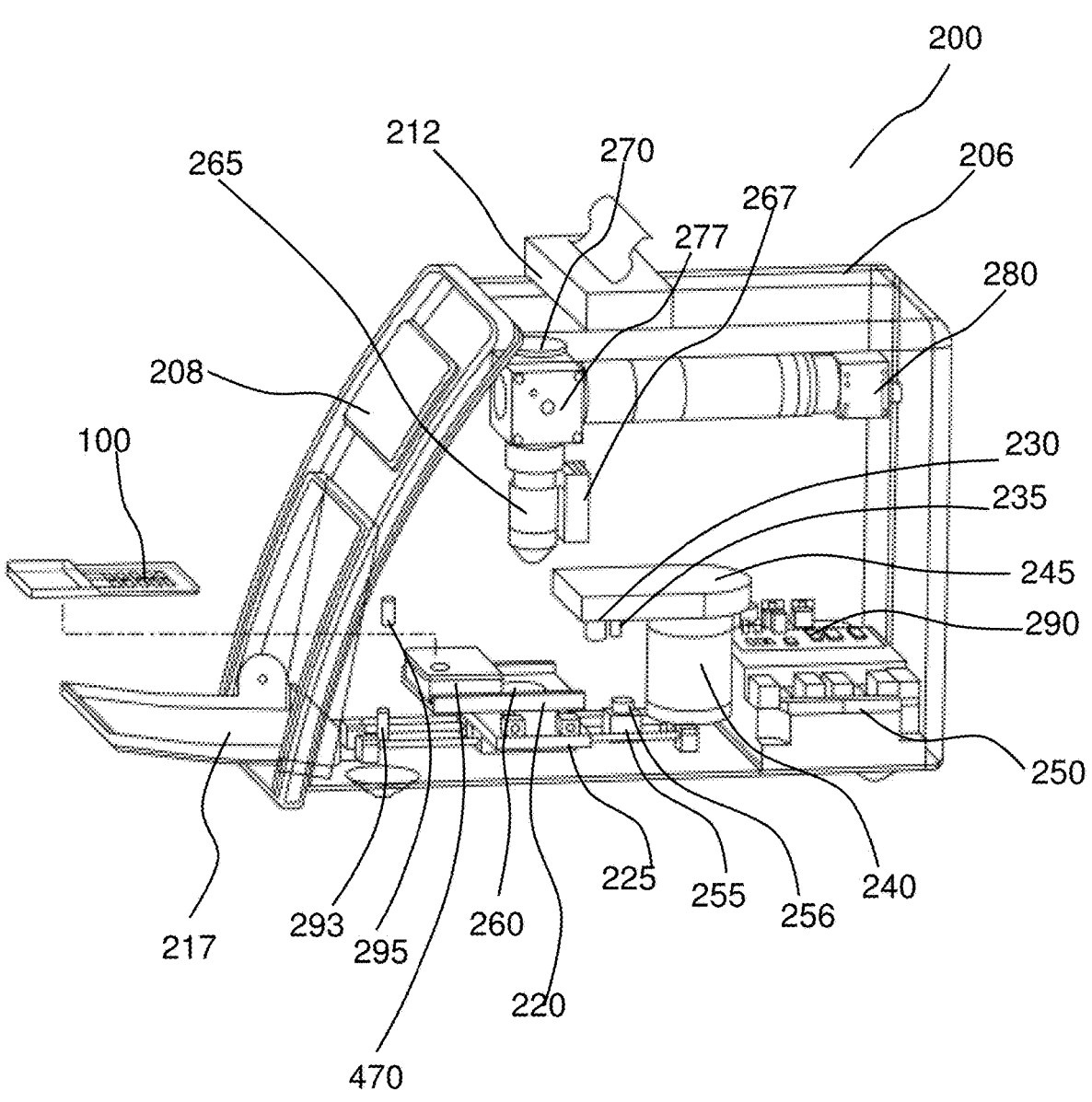
FIG. 3 is a cut-away view of an illustrative cell analyzer showing internal components with a test cartridge being inserted.

FIG. 2A shows test cartridge 100 with closure 135 shown in the open position to provide access to input port 130. Closure 135 is adapted to slide relative to the test cartridge 100 and may have detent or other positioning features that facilitate placing it in different positions. After the biological sample has been collected into input port 130, closure 135 may be moved to the position shown in FIG. 2B to cover the input port 130. The closure 135 may be moved by the user prior to inserting it into the analyzer as shown in FIG. 3. Alternatively, closure 135 may be moved by an operation within the cell analyzer. Alternate embodiments of closure 135 may include graphics, identifying information, or instructions to the user. While the closure 135 is illustrated as a sliding component, other means of closing the input port 130 are contemplated including a cap that hinges upward, a small surface cover that swivels away from and returns to cover the input port 130, or an adhesive component that sticks to the input port 130 or area surrounding it. In all cases the closure 135 includes a vent or air path to the input port to allow the blood sample to move into the test cartridge 100.

FIG. 3 is a cut-away view of an illustrative cell analyzer 200 with test cartridge 100 positioned so that the operator can introduce it into the analyzer. From the outside of the cell analyzer 200, one can see the housing 206, a user-interface screen 208, a printer 212, and a cartridge loading door 217. When the cartridge loading door 217 is opened, the test cartridge 100 can be placed on a cradle 220 of x-y stage 225, configured to receive test cartridge 100 from the user. The cradle 220 provides mechanical alignment of the cartridge to facilitate connections that are made between the analyzer and the cartridge. For example, a mechanical presser foot 230 may be placed in contact with a flexible surface on the test cartridge to provide mechanical pressure onto packaged, on-board reagents. Some embodiments of the cell analyzer 200 may utilize a reagent supply module 470 as further described with reference to FIG. 6. Reagent supply module 470 may be installed on x-y stage 225 and has a receiving area 473 (see FIG. 6) to provide alignment of the test cartridge 402 with the reagent module 470.

A valve driver 235 can be positioned to operate a rotary valve on the test cartridge. A vacuum/pressure pump 240 supplies negative or positive pressure to a manifold 245, which interfaces with the test cartridge 100 when it is placed in the cell analyzer as described below. The cell analyzer 200 further includes system controller 250 to control movement of the fluids in the test cartridge by activating the vacuum/ pressure pump 240, moving the mechanical presser foot 230, or operating the valve driver 235 according to pre-programmed sequences. Monitoring camera 255, positioned to acquire digital images of the fluids in the cartridge, provides feedback for the system controller 250. Monitoring light source 256 may be a ring illuminator that surrounds the lens of the monitoring camera 255. Information from the monitoring camera 255 is used to provide feedback for controlling movement of liquids, for positioning the rotary valve, and for confirming critical steps.

Also shown in FIG. 3 are the components that comprise the automated microscope of the cell analyzer 200. At the base of the analyzer, bright-field light source 260 provides illumination through the test cartridge to the objective lens 265, operatively coupled to focusing mechanism 267. At the top of the analyzer, fluorescent light source 270 provides illumination through dichroic mirror 277 to provide fluorescent excitation of the sample. At the rear of the analyzer, digital camera 280 captures images of the test cartridge 100 and transmits them to image processor/computer 290. In some embodiments, the cell analyzer may further include a photometric light source 293 and photometric detector 295 for measuring light transmission at one or multiple wavelengths in a chamber in test cartridge 100, such as for measuring hemoglobin, as is more fully explained below.

Figure 4:
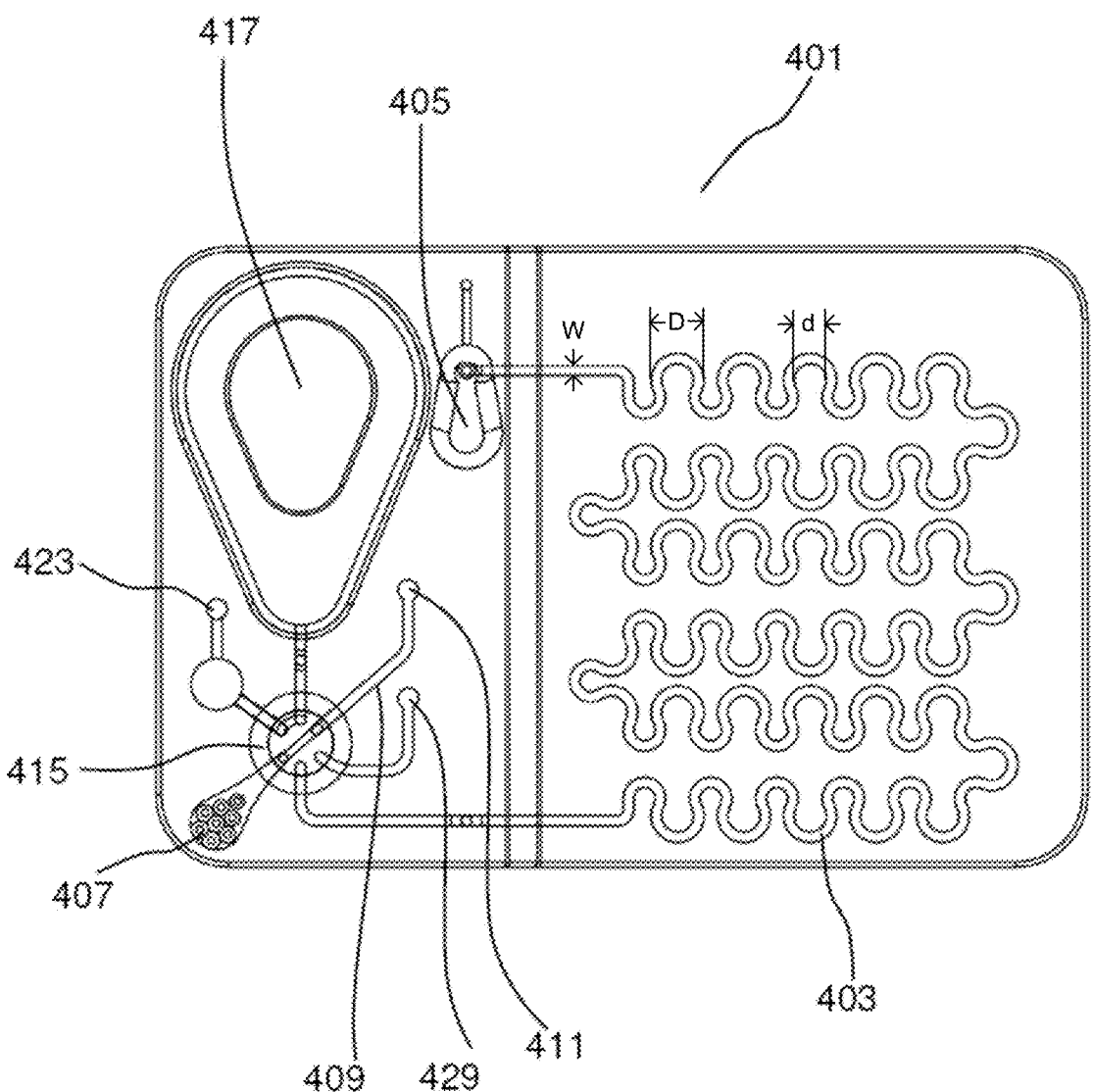
FIG. 4 is a plan view of an illustrative test cartridge of the type that includes reagents for conducting a test.

FIG. 4 shows an illustrative test cartridge 401 of the type that includes liquid reagents stored in a blister pack 417 for conducting a test. The test cartridge 401 has an input port 407 for receiving a sample, a passive mixing chamber 405 for mixing the sample with diluent/reagent, and an imaging chamber 403 for capturing images of the cells in the mixture of sample and diluent/reagent for analysis. In this embodiment, photometric chamber 409 may be filled with whole blood to make optical absorbance measurements to determine concentrations of certain analytes in the sample, such as hemoglobin. A rotary valve 415 provides fluidic connections between various fluidic channels, vents, and ports, including sample driver port 411, vent 423 and mixture driver port 429 as will be described in FIGS. 8A-8F.

Figure 5:
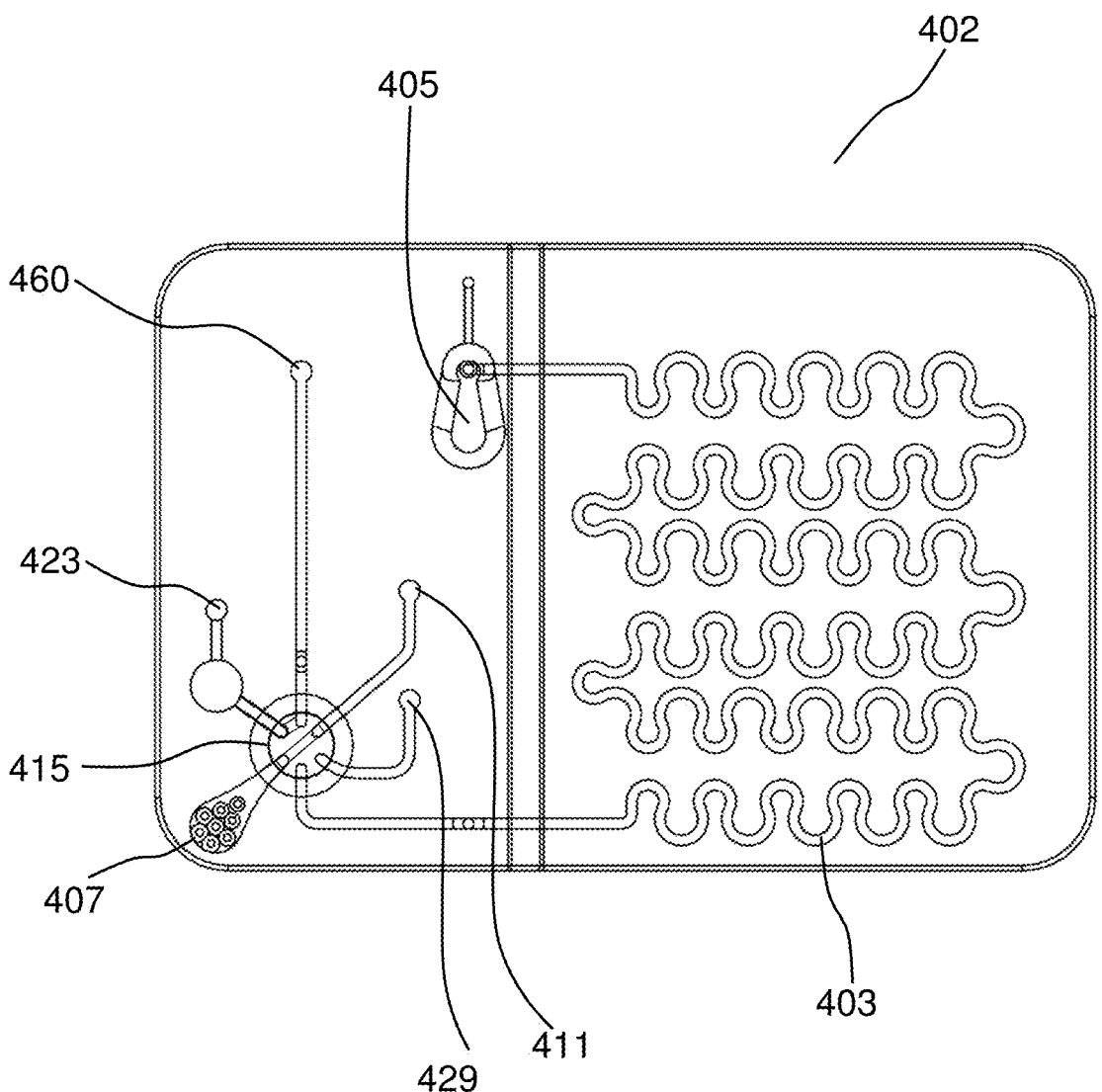
FIG. 5 is a plan view of an illustrative test cartridge of the type that does not include reagents.

FIG. 5 shows an illustrative test cartridge 402 of the type that does not include on-board diluent/reagents. Many of the functional components are identical to those illustrated with reference to test cartridge 401, but instead of on-board diluent/reagents, test cartridge 402 has a reagent input port 460 adapted to be connected to an external source of diluent/reagent. Test cartridge 402 may be used in embodiments in which diluent/reagents that are needed for an analysis may be too costly to package individually or may require refrigerated storage. In such an embodiment, diluent/reagent may be provided from a source within cell analyzer 200 or from a reagent supply module.

Figure 6:
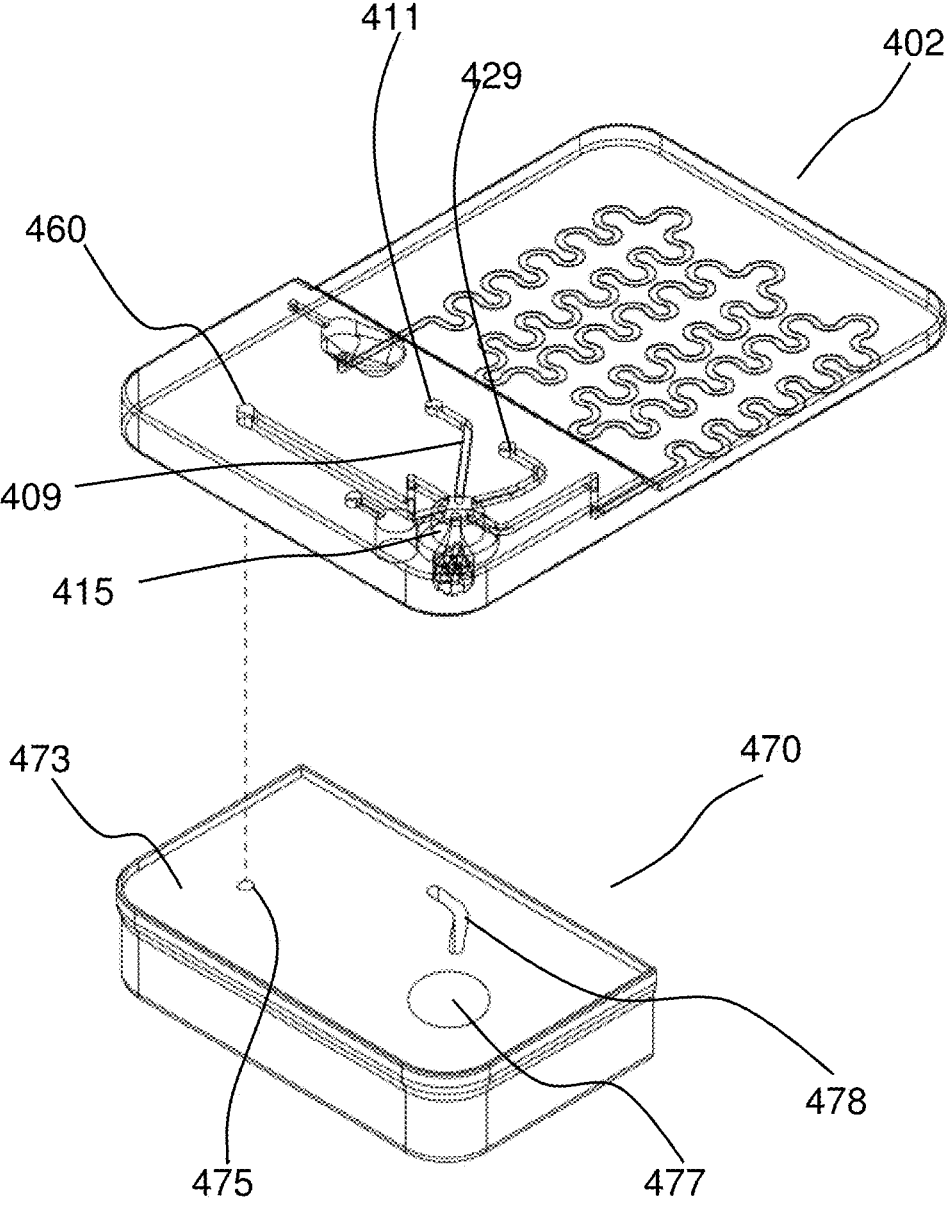
FIG. 6 is a perspective view of an illustrative reagent supply module showing a test cartridge ready to be joined with the module.

FIG. 6 shows an illustrative reagent supply module 470 positioned to receive test cartridge 402. The reagent supply module 470 includes a receiving area 473 for docking the test cartridge 402, and contains a vessel for holding the diluent/reagent, a reagent metering pump adapted to pump the diluent/reagent, and a reagent output port 475. The reagent output port 475 is constructed with a suitable shape and/or elastomeric materials to insure a liquid-tight connection to reagent input port 460 on the test cartridge 402, when the test cartridge is docked to the reagent supply module 470. Reagent supply module 470 has an opening 477 suitably sized to allow monitoring camera 255 (FIG. 3) to image the rotary valve 415. Additionally a window 478 in the reagent supply module 470 is constructed to align with the photometric chamber 409 in the test cartridge. Window 478 allows the photometric light source 293 and photometric detector 295 (FIG. 3) to make optical absorbance measurements on the fluid within photometric chamber 409.

In one embodiment, the size of the vessel within reagent supply module 470 is of sufficient capacity to provide diluent/reagents to dilute and/or stain from ten to about one-hundred samples with a diluent/reagent to sample ratio of 10:1 to about 250:1. The reagent supply module 470 further can include a self-priming mechanism for priming the liquid reagent and eliminating air bubbles. In such an embodiment, the reagent supply module 470 may include a chamber for collecting waste reagent from the priming process. Once the test cartridge 402 is docked with the reagent supply module 470 the combined pieces perform the same functions as test cartridge 401 except that the reagent supply module 470 replaces the blister pack 417. Inside cell analyzer 200 the vacuum/pressure pump 240 makes connections through manifold 245 to sample driver port 411 and mixture driver port 429. The interfaces between the manifold 245 and these ports are constructed with a suitable shape and/or elastomeric material to ensure an airtight connection so that system controller 250 can control movement of the fluids in the test cartridge (see FIG. 3). In such an embodiment the presser foot 230 is not needed.

Figure 7A:
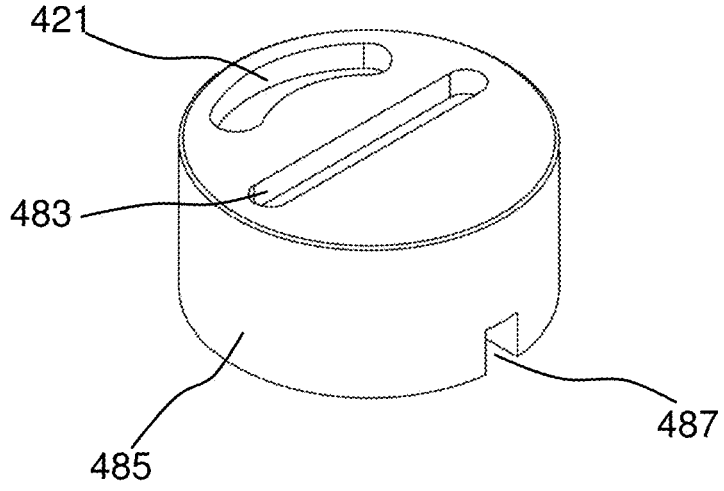
FIG. 7A is a perspective bottom view of a metering chamber formed in the face of a valve stem of a rotary valve.
Figure 7B:
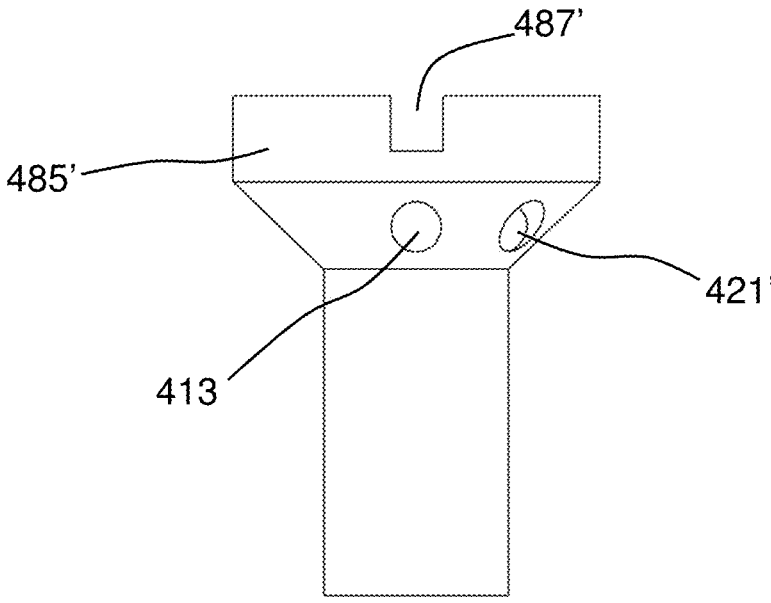
FIG. 7B is a side view of a valve stem with a metering chamber formed as a pass-through conduit.

The only volume that is measured precisely is the metered volume of the original biological sample. Various means for metering a small volume of liquid are well known in the art. Two devices that are well suited for low cost, single use applications according to the present invention are shown in FIG. 7A and FIG. 7B. FIG. 7A shows the face of a cylindrical valve stem 485 of a rotary face valve. Metering chamber 483 is formed in the face by highly precise manufacturing processes such as injection molding. The chamber 483 is narrow and tubular in shape and centered in the face of the cylindrical stem 485. A slot 487 in the top of stem 485 acts as a valve indexer to indicate the position of the valve stem 485. Also formed in the face of valve stem 485 is an auxiliary connector 421, which has a circular shape. When assembled into the rotary valve 415 (FIGS. 4 and 5), metering chamber 483 is able to connect between ports in the valve which are 180 degrees apart, while auxiliary connector 421 connects between other ports which are 60 degrees apart. As will be explained with reference to FIG. 8A-8F, system controller 250 is able to control movement of the fluids by rotating valve stem 485 and by positioning the valve according to the valve indexer 487 according to preprogrammed sequences. Thus in a first position, the metering chamber 483 can be connected to the input port 407 (FIG. 4 and FIG. 5) and filled with the biological sample, and then by rotating valve stem 485, the volume contained within metering chamber 483 can be isolated and transferred for analysis.

FIG. 7B is a side view of a valve stem 485' with a metering chamber formed as a pass-through conduit 413 in the tapered seat of valve stem 485'. Pass-through conduit 413 is able to connect with fluidic channels in rotary valve 415 which are 180 degrees apart. Also shown in FIG. 7B is auxiliary fluidic connector 421', which provides connections to adjacent fluidic channels which are 60 degrees apart.

When assembled in the rotary valve 415 (FIG. 4 and FIG. 5) having a tapered seat to receive valve stem 485', pass-through conduit 413 can be connected to input port 407 (FIG. 4 and FIG. 5), filled with the biological sample, and then by rotating valve stem 485', the volume of sample contained within pass-through conduit 413 can be isolated and transferred for analysis. FIG. 7B also shows auxiliary fluidic connector 421', which provides fluidic connections to adjacent fluidic channels on the test cartridge according to the position of the valve indexer 487'. It will be appreciated that the rotary face valve of FIG. 7A and the tapered seat valve of FIG. 7B are alternate embodiments for isolating sample and controlling fluidic paths. Therefore, in the descriptions that follow references to metering chamber 483 in a rotary face valve will be equally applicable to pass-through conduit 413 in a tapered seat valve.

Figure 8A:
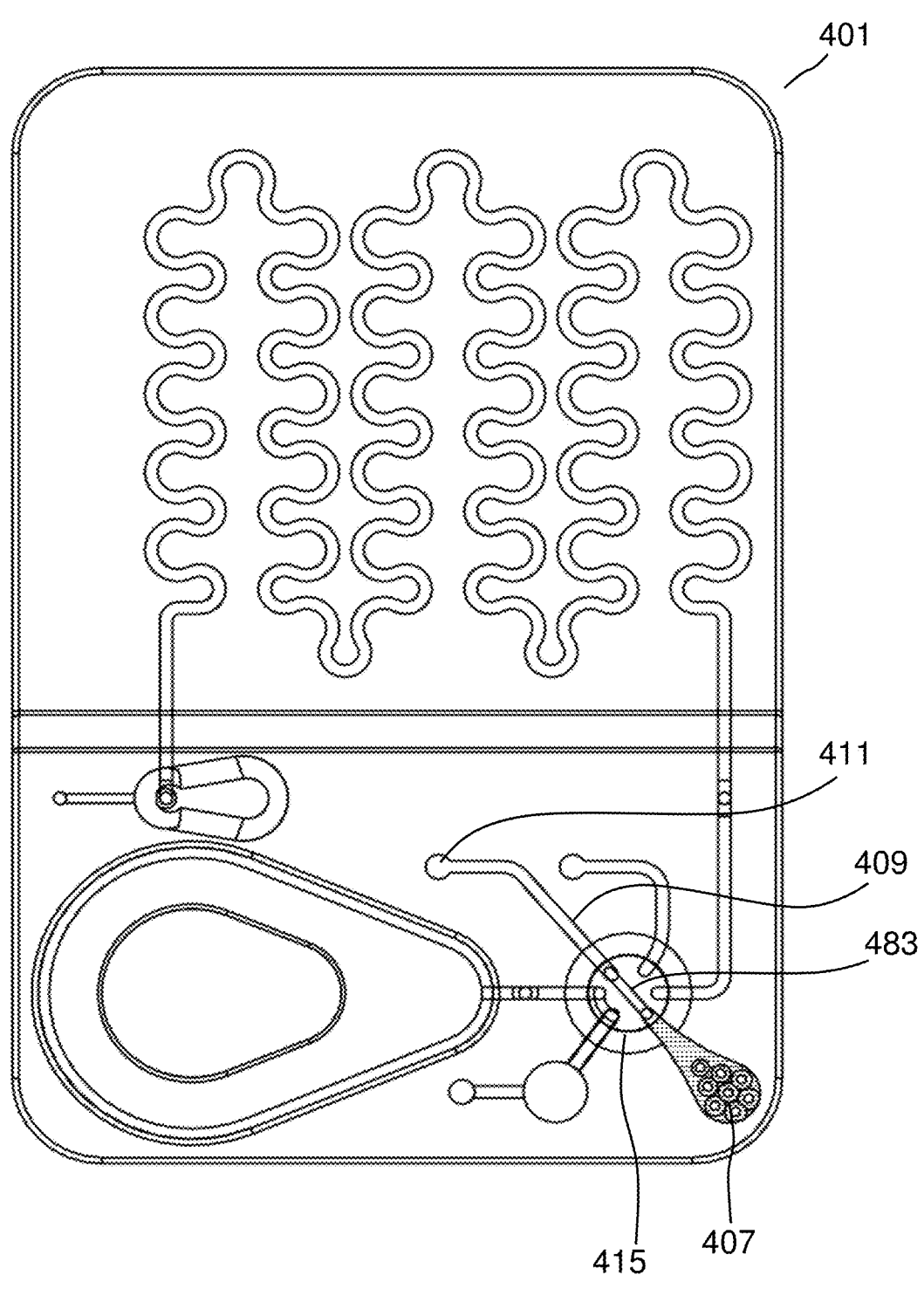
FIG. 8A is a plan view of an illustrative test cartridge showing a sample of whole blood deposited in the input port area.

Now turning our attention to FIGS. 8A through 8F, and with reference to FIG. 3, a sequence of operations will be illustrated that enable cell analyzer 200 to perform automated microscopic cell analysis on a biological sample without skilled operator interactions. In FIG. 8A a sample is shown deposited into input port 407, which is in fluid communication with rotary valve 415. As illustrated in FIG. 8A, the stem 485 (FIG. 7A) of rotary valve 415 is in a first position wherein the metering chamber 483 (FIG. 7A) is aligned with the sample input port 407 and the sample driver port 411. A vacuum, supplied by the analyzer to sample driver port 411, draws the sample from the input port 407 into the metering chamber 483 and into the photometric chamber 409. When the photometric chamber 409 has been filled with sample, the system controller 250 (FIG. 3) collects absorbance data from the undiluted sample using the photometric light source 293 (FIG. 3) and photometric detector 295 (FIG. 3). As will be understood by those skilled in the art, suitable choice of optical wavelengths and chamber geometry and analysis of the light passing through the biological sample can be used to determine concentrations of certain analytes in the sample such as hemoglobin.

Figure 8B:
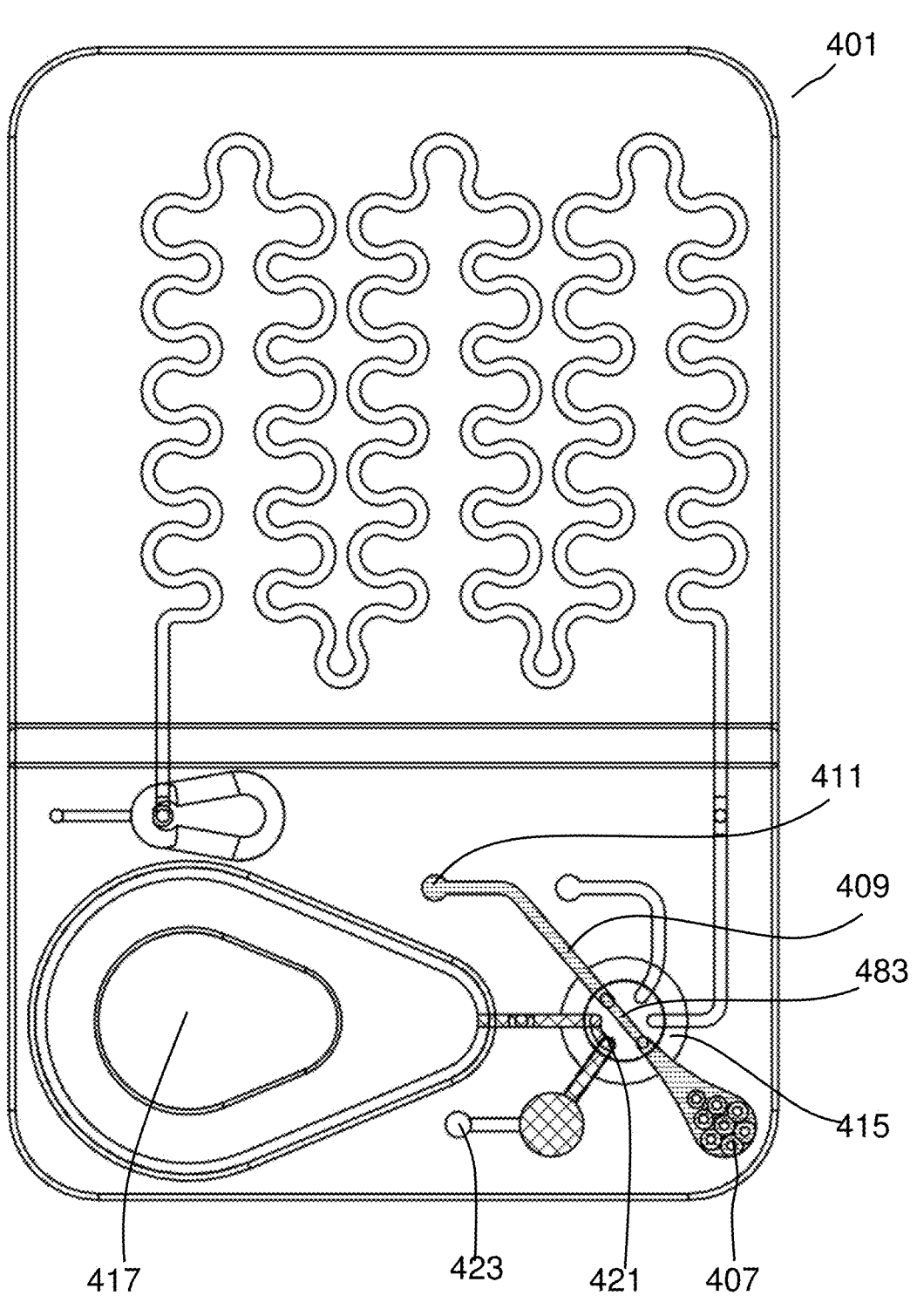
FIG. 8B is a plan view of the test cartridge of FIG. 8A showing initial movement of the sample and reagent with the rotary valve in the first open position.

By illustration and with reference to FIG. 8B, cartridge 401 is shown with a diluent/reagent contained in a blister pack 417. When rotary valve 415 positioned such that the metering chamber 483 is aligned with the input port 407 and photometric chamber 409, auxiliary connector 421 provides a fluid communication path between the blister pack 417 and vent 423. When pressure is applied to the blister pack 417 by presser foot 230 (FIG. 3), diluent/reagent is released and flushed through auxiliary connecter 421 thereby priming the channels and removing air bubbles through vent 423.

Figure 8C:
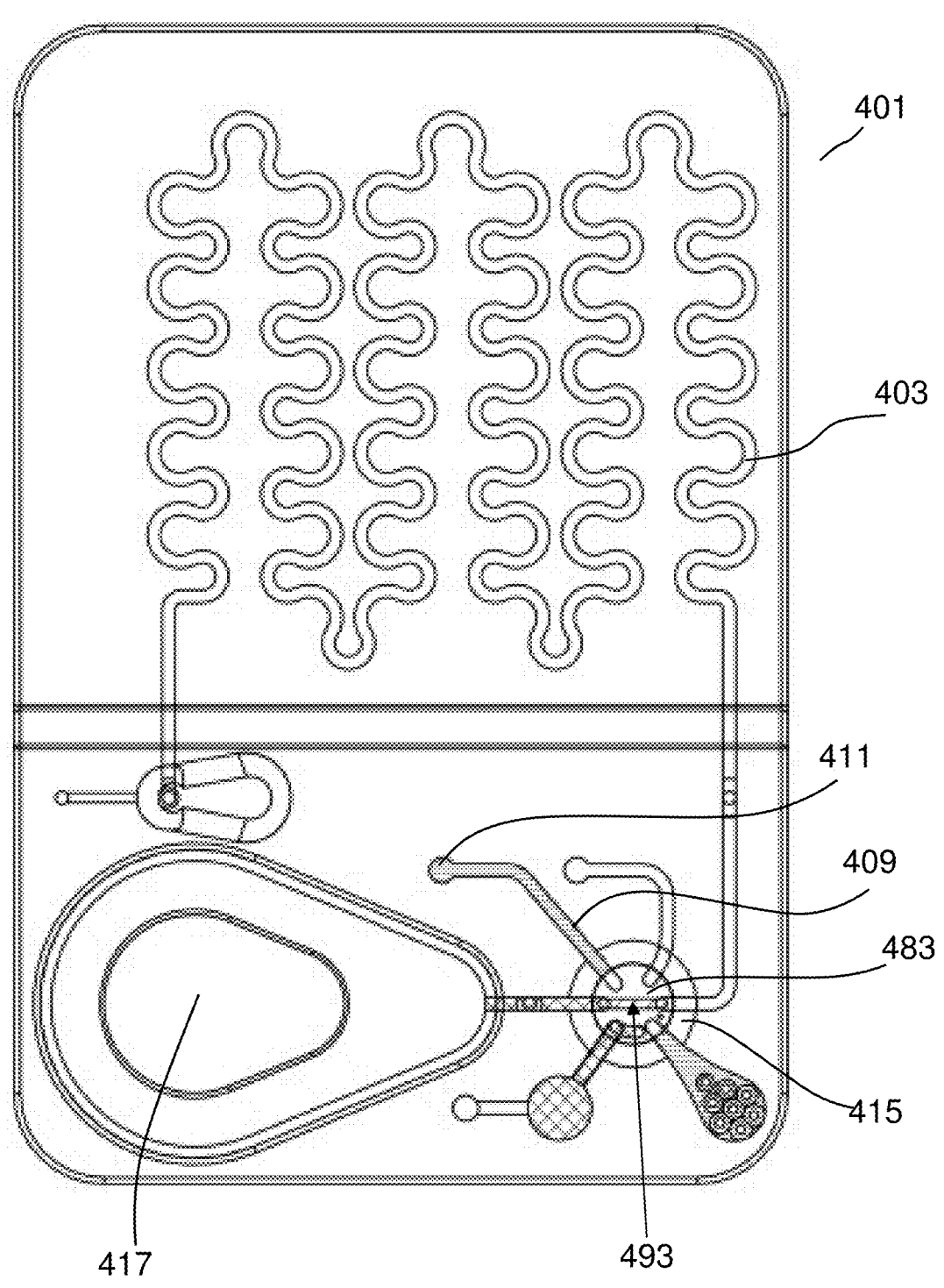
FIG. 8C is a plan view of the test cartridge of FIG. 8B with the valve in the second open position.

FIG. 8C shows rotary valve 415 turned counterclockwise 60 degrees to a second position, which isolates a predetermined amount of sample in the metering chamber 483. In this second position the stem 485 of rotary valve 415 is positioned such that the metering chamber 483 is in fluid communication with blister pack 417 and the serpentine imaging chamber 403.

Figure 8D:
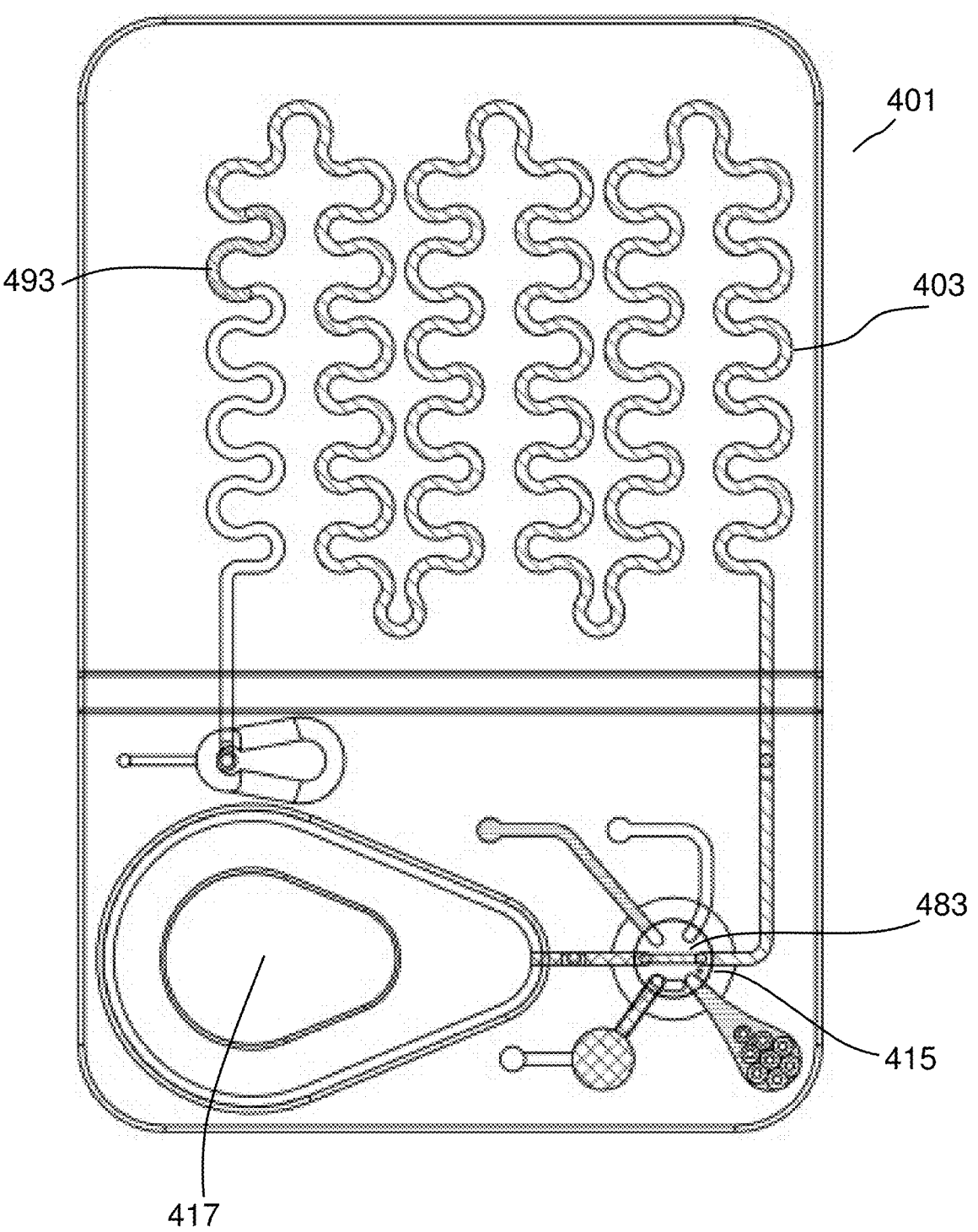
FIG. 8D is a plan view of the test cartridge of FIG. 8C illustrating the sample and the reagent in the imaging chamber.

In FIG. 8D, the rotary valve 415 is shown in the same position as in FIG. 8C but following operation of the presser foot 230 which applies pressure to the blister pack 417. As illustrated by the shaded area, the diluent/reagent from blister pack 417 and the isolated sample 493 from the metering chamber 483 are transferred into the imaging chamber 403. A minimum volume of reagent of three times the volume of the pass-through conduit 413 is needed to flush the entire sample from the rotary valve 415. According to the analysis being conducted, a sufficient volume of the reagent is pushed through the rotary valve 415 to completely wash out the isolated sample and to achieve the approximate dilution ratio desired.

Figure 8E:
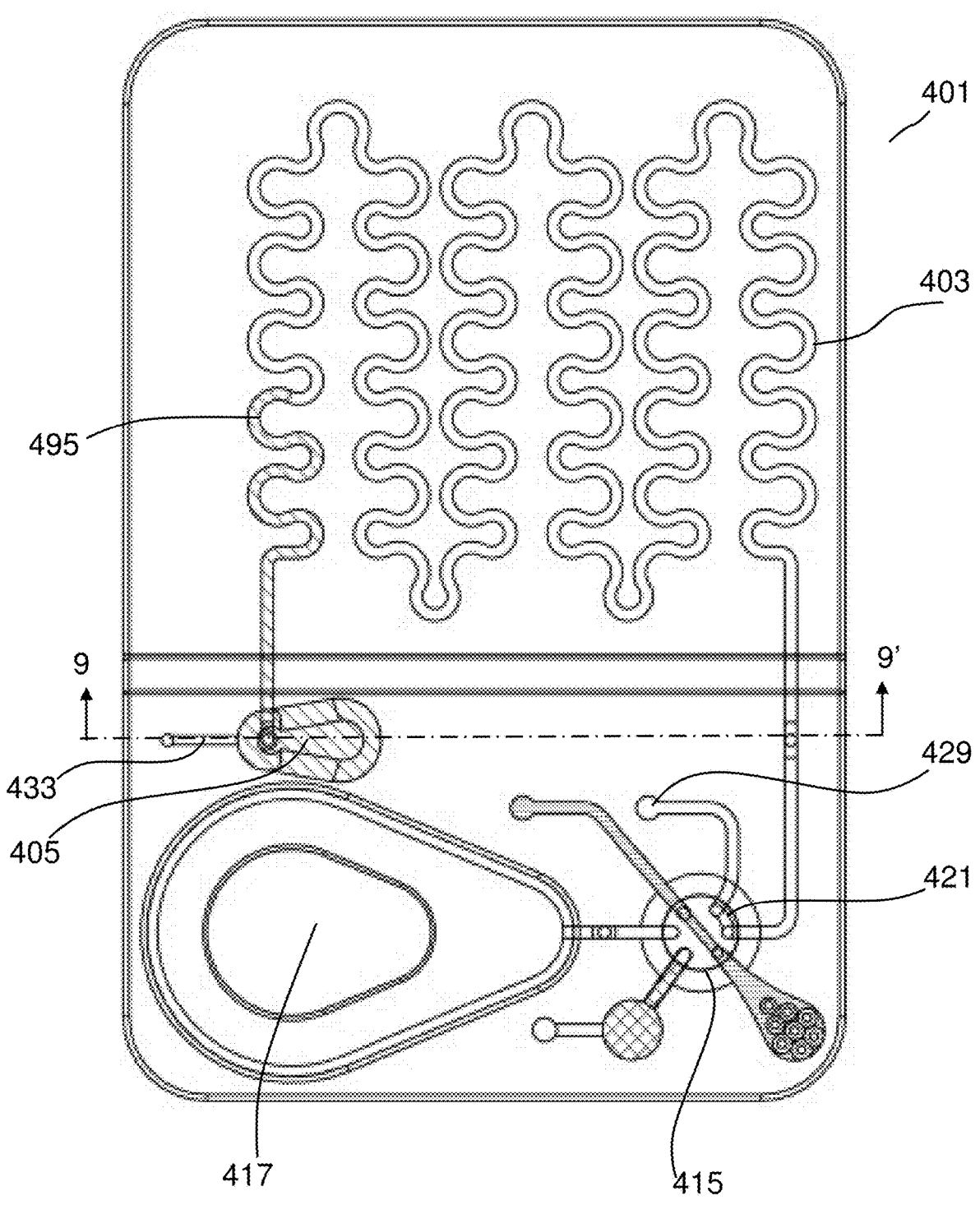
FIG. 8E is a plan view of the test cartridge of FIG. 8D illustrating the sample and most of the reagent positioned in the mixing chamber.

In FIG. 8E the rotary valve 415 is shown turned counterclockwise 120 degrees from its previous position shown in FIG. 8D to its third position, wherein auxiliary connector 421 is aligned with mixture driver port 429 and imaging chamber 403. Vacuum/pressure pump 240 of cell analyzer 200 (FIG. 3) supplies pressure to mixture driver port 429 and pushes all of the mixture of sample and diluent/reagent from the imaging chamber 403 into passive mixing chamber 405.

Figure 8F:
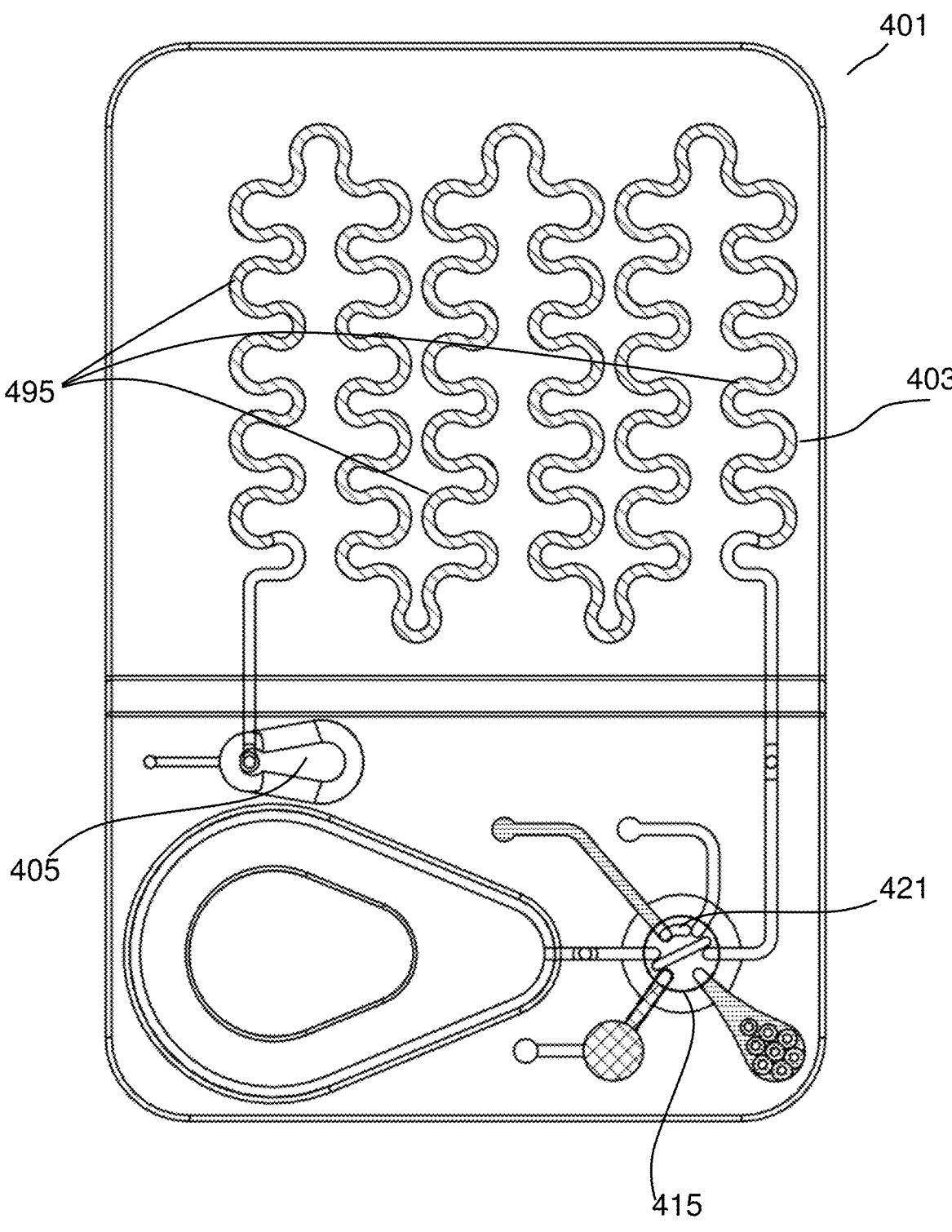
FIG. 8F is a plan view of the test cartridge of FIG. 8E illustrating all of the sample and the reagent positioned in the imaging chamber and the valve in a final, closed position.

As the mixture enters passive mixing chamber 405, air within the chamber is vented through vent port 433. Once all of the mixture of sample and diluent/reagent has been transferred to the passive mixing chamber 405, vacuum/pressure pump 240 applies a controlled vacuum to mixture driver port 429 such that the mixture is pulled back into the imaging chamber 403. A preprogrammed sequence of pushing the mixture into the passive mixing chamber 405 and pulling it back into the imaging chamber 403 is repeated to achieve a final mixture 495 that is free from cell clumping and overlapping after the cells settle to the bottom of the imaging chamber 403. In the final movement of the mixture 495, it is positioned entirely within the imaging chamber 403 as illustrated in FIG. 8F. We have found that that in most instances, pushing the sample and diluent/reagent into mixing chamber 405 and pulling it out is sufficient to provide a uniform mixture. Further, the mixture remains substantially uniform when it is transferred into serpentine imaging chamber 403. It should also be noted that the mixing chamber 405 could be located at the beginning of the imaging chamber 403.

FIG. 8F illustrates the final step of the sample preparation sequence. At this point in the preprogrammed sequence, the entire final mixture 495 has been withdrawn from the passive mixing chamber 405 and is positioned in the imaging chamber 403. When this position is achieved, the rotary valve 415 is rotated counterclockwise approximately 30 degrees to the position shown in FIG. 8F, whereby it is not in fluid communication with any fluidic channel in rotary valve 415, thereby blocking further fluid communication with the imaging chamber 403 so that no further movement of the final mixture 495 can take place.

Figure 9:
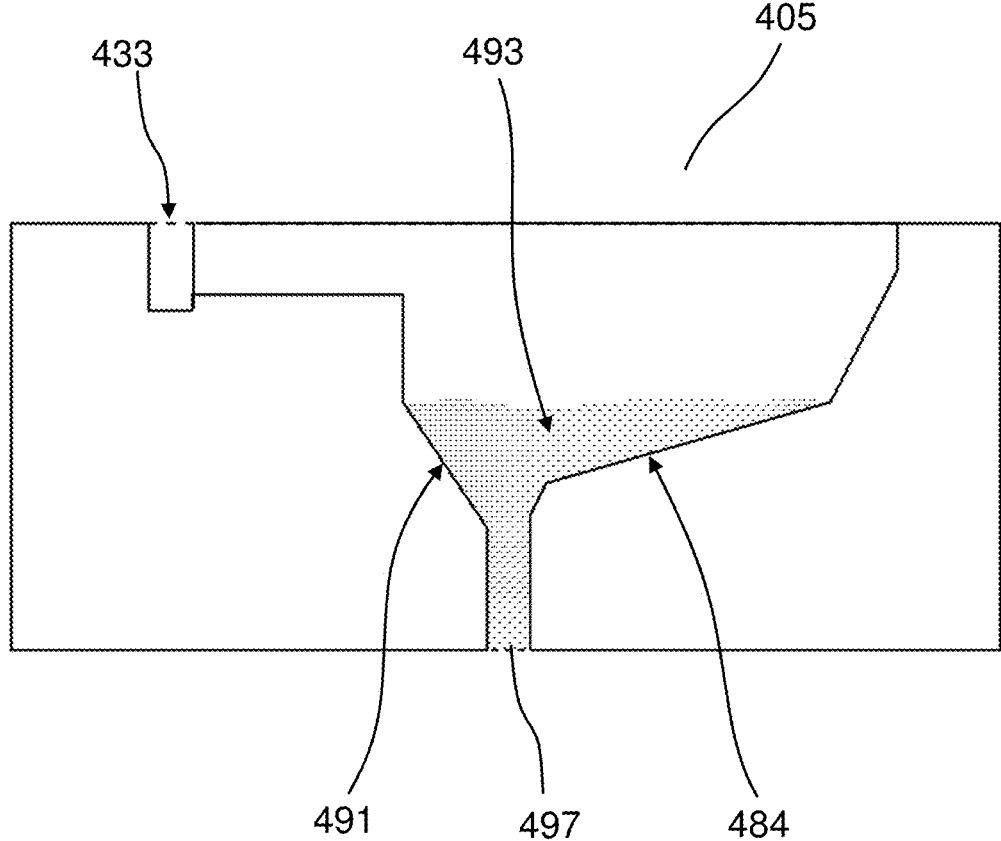
FIG. 9 is an side elevation view of a cross section of the passive mixing chamber taken through line 9-9' of FIG. 8E.

FIG. 9 shows a cross section of the passive mixing chamber 405. The chamber is referred to as "passive" because as illustrated, it does not contain any active mixing element such as a bead or spin-bar. Such devices may be used in some embodiments, but we have found that an adequately sized chamber as depicted in FIG. 9 is simpler and provides excellent mixing of the sample and reagent. In operation the diluent/reagent and sample 493 are driven by vacuum/pressure pump 240 (FIG. 3) and enter and exit the chamber through mixing chamber opening 497. As liquid enters the chamber, air within the chamber escapes through vent port 433. The cross section of passive mixing chamber 405 illustrates wall geometry that increases smoothly in size from the bottom to the top such that the mixture entering from below expands into a larger volume. The chamber 405 may have asymmetrical sloped walls 484 and 491 to promote mixing of the sample and reagent and for removing bubbles from the mixture. After all of the mixture is in the chamber, air bubbles may be introduced to the chamber by vacuum/pressure pump 240 through mixing chamber opening 497. These air bubbles further promote mixing and subsequently escape through vent port 433. The choice of materials used to fabricate the passive mixing chamber 405 should take into consideration the wetting properties of the specific 1 diluent/reagent(s) being utilized in the test cartridge 401. The properties of the material, among other requirements, should ensure that liquid surface tension will pull back all of the liquid in contact with the side walls of the chamber when the vacuum/pressure pump 240 empties the chamber through mixing chamber opening 497.

Figure 10:
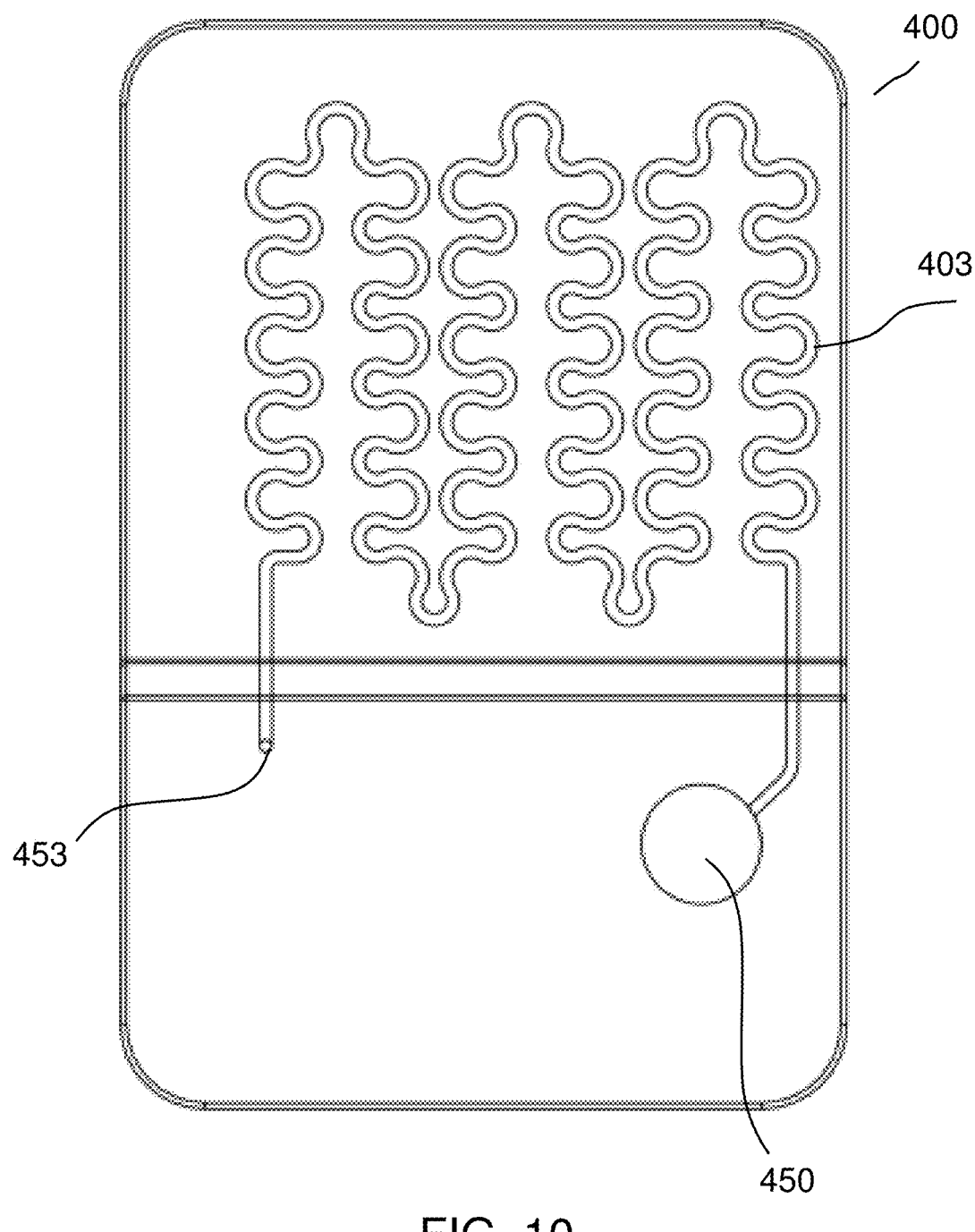
FIG. 10 is a plan view of a test cartridge of an alternate test cartridge embodiment.

FIG. 10 illustrates test cartridge 400 which comprises an imaging chamber 403 having at one end a sample input port 450, and at the opposite end a vent 453. A user of test cartridge 400 collects a small known volume of whole blood and mixes it manually with a diluent/reagent in a separate single-use sample preparation device (not shown). Once mixed, the entire mixed volume is injected into sample input port 450. Air escapes through vent 453 as the mixture is injected allowing the sample to fill the imaging chamber 403. The imaging chamber is essentially the same imaging chamber as described above and shown in FIGS. 8A-8F. Test cartridge 400 can be placed into analyzer 200 (FIG. 3) for analysis beginning at step 560 of FIG. 11 as described below.

Figure 11:
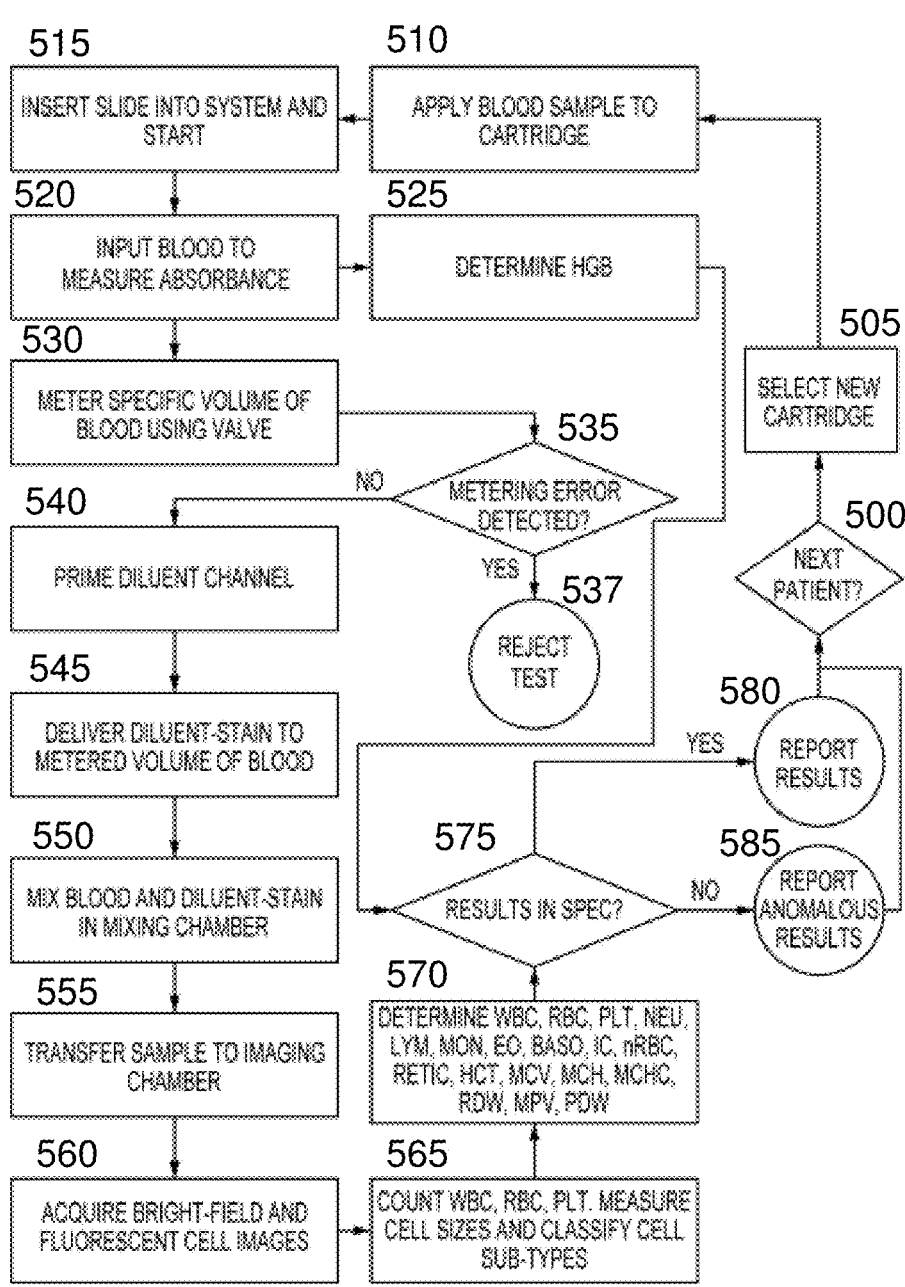
FIG. 11 is a flowchart illustrating the operation of the cell analyzer.

Turning our attention to FIG. 11 we will now describe the overall operation of cell analyzer 200 configured to provide a "CBC with Differential" analysis with reference to the test cartridge 401 illustrated in FIGS. 8A-8F and cell analyzer 200 illustrated in FIG. 3. To obtain the blood sample from a patient presented at box 500, the user first obtains a new test cartridge 401 at box 505 and opens it to expose the input port 407. Blood from a finger prick is applied as illustrated in FIG. 1 at box 510 and the input port 407 is covered. The user inserts the test cartridge into the cell analyzer 200 at box 515. The test cartridge is moved into the analyzer where mechanical and fluid connections are made between the analyzer and the cartridge as described above with reference to FIG. 3. As a first step of analysis, the sample is drawn into the metering chamber passing through and into photometric chamber 409 (FIG. 8A). Absorbance of the blood is measured at box 520. Data from absorbance measurements are used to determine hemoglobin concentration. At box 530 sample in the metering chamber 483 is imaged using monitoring camera 255 and analyzed to confirm that the metering chamber was properly filled at box 535. If an error is detected the analysis is terminated at box 537 and the user is alerted to the error and instructed to remove the cartridge and reject the test.

If the pass-through conduit 413 is correctly filled the diluent/reagent channel is primed at box 540 as described above with reference to FIG. 8B. Rotary valve 415 is then turned to the position shown in FIG. 8C to isolate the sample and to allow diluent/reagent to wash the metered volume of blood out of the pass-through conduit 413 at box 545 while being imaged by monitoring camera 255. The transfer continues until the monitoring camera 255 confirms that diluent/reagent plus sample has almost filled the imaging chamber as illustrated in FIG. 8D.

Once a sufficient volume of diluent/reagent is transferred, rotary valve 415 is positioned as shown in FIG. 8E and the total volume of sample and diluent/reagent is mixed at box 550. At box 555 the entire volume 495 is transferred to the imaging chamber and rotary valve 415 is positioned as shown in FIG. 8F. Note that by transferring the entire volume of mixed sample 495, all of the metered volume of blood from the original sample plus the unmetered volume of diluent/reagent is positioned in the imaging chamber at box 555.

If test cartridge 400 is used, it is inserted into cell analyzer 200 and analysis begins at step 560. Analysis of test cartridge 401 or 402 continues at step 560 when the x-y stage 225 moves the test cartridge 401 to obtain bright-field and fluorescent images of the entire imaging chamber 403 at box 560. In an alternate embodiment, objective lens 265 and/or digital camera 280 are moved and test cartridge 401 remains stationary. In yet another embodiment objective lens 265 has sufficient field of view to capture the entire imaging chamber 403 without movement. Two digital images of each physical frame of the imaging chamber are transferred to image processor/computer 290 at box 565. One image, taken with bright-field optics, can be compared to the other image taken with fluorescent optics to identify red blood cells, white blood cells and platelets. Further analysis of the white cell sizes and internal structure can identify sub-types of white cells using pattern recognition.

At box 570 comparison of the bright-field and fluorescent images can differentiate mature red cells from reticulocytes and nucleated red blood cells. By dividing each cell count by the known volume of the metering chamber 483, the concentration (cells per unit volume) can be determined. By using a sphering agent the planar sizes of red cells can be transformed into mean corpuscular volume (MCV). Combining the red blood cell count with MCV and the volume of the metering chamber 483 allows the calculation of hematocrit (HCT) and red cell distribution width (RDW). Further calculations using the separately measured HGB from box 525, combined with the RBC count gives mean corpuscular hemoglobin (MCH), and mean corpuscular hemoglobin content (MCHC).

At box 575 the measured results are compared with previously defined limits and ranges for the particular patient population and determination is made whether the results are within or outside normal expected ranges. According to this determination results within normal ranges are reported in box 580 and results that are outside the normal ranges are reported in box 585.

EXAMPLES

Example 1: Information from Bright-Field and Fluorescent Optics

Figure 12A:
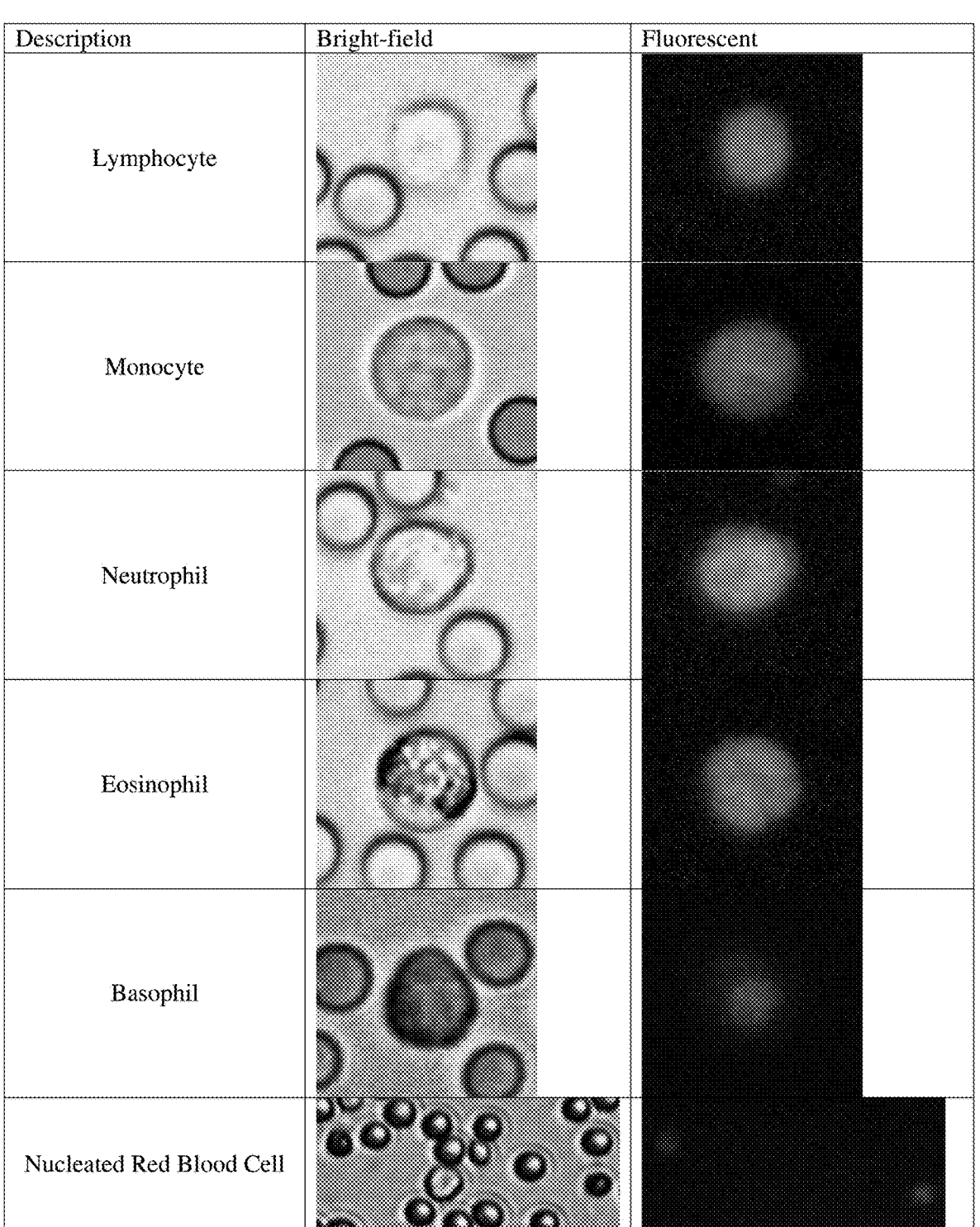
FIGS. 12A and 12B show both bright-field and fluorescent images of the same cells that were collected according to the present invention.
Figure 12B:
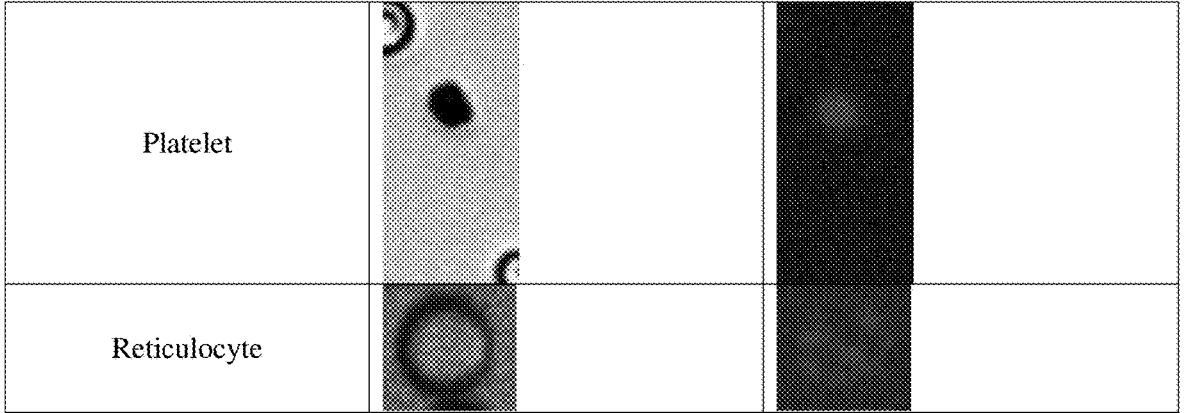

FIG. 12 shows images that were collected using test devices according to the present invention. A fluorescent stain Acridine Orange (AO) was used to differentially stain DNA and RNA of cells in a whole blood sample. The visual images of FIG. 12 were obtained using an Olympus 20X× 0.4 NA objective lens 265 and a Basler 5 MP digital camera 280. Excitation of the bright-field images in the second column was provided by white light bright-field source 260. Excitation of the fluorescent images in the third column was a 455 nm blue fluorescent light source 270.

White blood cells have significant RNA and DNA and therefore can be seen in the fluorescent images having green and orange structures. The size and shape of the green nuclear structure and overall size of the white cells can be used to differentiate them into sub-groups identified by name in the first column. Notably the basophil and eosinophil sub-groups of white cells have characteristic features in the bright-field image due to the presence of large granules in the cytoplasm. Therefore embodiments of the present invention make use of both bright-field and fluorescent image analysis to differentiate sub-groups of white cells.

Platelets also take up the AO stain but the size of a platelet is significantly smaller than any white cell and can therefore be differentiated. Because red cells lose their nucleus as they mature, they do not have nuclear material to take up the AO stain. Consequently the red cells can be identified as the objects that appear in the bright-field and cannot be seen in the fluorescent field. The immature red cells, called reticulocytes and the nucleated red blood cells (nRBC) have attributes of red cells but also show small levels of fluorescence. Embodiments of the present invention make use of these combined attributes to identify and sub-group red blood cells.

Example 2. Statistical Sampling of the Imaging Chamber

Table 1 illustrates a comparison of CBC parameters obtained according to the present invention and from an automated hematology analyzer.

TABLE 1

| Column1 | # pairs | RBCs | WBCs | ROI | RBC/f | RBC/f(%)- | WBC/f | WBC/f(%) | RBC/WBC |
|---|---|---|---|---|---|---|---|---|---|
| 100% | 9916 | 2455492 | 5125 | 3818.7 | 643.02 | 100.0 | 1.342 | 100.0 | 479.12 |
| 50% | 4958 | 1229669 | 2535 | 1913.7 | 642.56 | 99.9 | 1.325 | 98.7 | 485.08 |
| 25% | 2479 | 623048 | 1285 | 968.5 | 643.28 | 100.0 | 1.327 | 98.9 | 484.86 |
| 10% | 992 | 242197 | 519 | 373.5 | 648.48 | 100.8 | 1.390 | 103.5 | 466.66 |
| 5% | 496 | 126186 | 262 | 197.2 | 639.82 | 99.5 | 1.328 | 99.0 | 481.63 |
| 1% | 100 | 23683 | 63 | 35.6 | 664.61 | 103.4 | 1.768 | 131.7 | 375.92 |

Sample: Low WBC count—approximately 2000/uL (normal is 3,000-10,000/uL).

Magnification: 20×

Number of images: approximately 10,000 bright-field and 10,000 fluorescent

Variable: Column 1—Percentage of total cells use in the calculation

Column #pairs—the number of pairs of images (bright-field plus fluorescent)

Column RBCs— total number of Red Blood Cells counted

Column WBCs— total number of White Blood Cells counted

Column ROI— total Region of Interest. This is the 'effective' number of image frames occupied by actual sample. A frame totally filled with sample/cells is "1". A partial frame (due to an edge or the curved ends of the serpentine shape), is a fraction of a frame (e.g. 0.567).

Column RBC/f—Average number of Red Blood Cells per frame (Column RBCs divided by Column 5 ROI).

Column RBC/f (%)— This is the RBC/frame value at a particular sampling percentage divided by the RBC/frame for the 100% sampling case (top line). This is an estimate of the accuracy of the particular sampling percentage compared to counting 100% of the cells.

Column WBC/f—Average number of White Blood Cells per frame (Column WBCs divided by Column ROI).

Column 9 WBC/f (%)— This is similar to Column 7 but estimates the accuracy of the sampling percentage for the White Blood Cells.

Column RBC/WBC— This is the ratio of RBC/WBC for the particular sampling percentage. Results: A small percentage of the total frames can provide accurate results. As a smaller fraction of the total frames are counted, the accuracy is maintained down to 1% for Red Blood Cells and down to 5% for White Blood Cells.

Discussion: In these experiments, it took approximately one second to capture an image pair. For this experiment, where almost 10,000 image pairs were needed to capture 100% of the sample, this means that image analysis took 10,000 seconds or approximately 2.8 hours. The experiment shows that the uniformity of the distribution of cells across the imaging chamber was good enough to provide accurate results by counting cells in only 5% of the frames. The goal of "counting every cell" is achieved because the entire sample size (the Region of Interest ROI) is measured, but only 5% of the images need to be analyzed to get accurate results. This reduces the image analysis time to approximately 8 minutes. It is expected that advances in camera and computer processing technology will further reduce this time.

The present invention has now been described in connection with a number of specific embodiments thereof. However, numerous modifications which are contemplated as falling within the scope of the present invention should now be apparent to those skilled in the art. Therefore, it is intended that the scope of the present invention be limited only by the scope of the claims appended hereto. In addition, the order of presentation of the claims should not be construed to limit the scope of any particular term in the claims.

What is claimed is:

1. A single-use cartridge for use with an apparatus that includes an automated microscope for analyzing cells in a biological sample, comprising:
   a) a sample collection port for receiving the sample,
   b) a metering chamber for holding a predetermined volume of the sample,
   c) a diluent channel configured to be in fluid communication with a liquid reagent,
   d) a mixing chamber,
   e) an imaging chamber adapted to allow images of the cells from the biological sample to be acquired by the automated microscope, and
   f) at least one movable valve mechanism configured to (1) create fluid communication in a first position between the sample collection port and the metering chamber, and (2) in a second position to create fluid communication between the sample contained in the metering chamber and the diluent channel, the imaging chamber and the mixing chamber;
   wherein the imaging chamber has sufficient volume to contain all of the predetermined volume of sample from the metering chamber when mixed with an unknown portion of the liquid reagent and has a depth such that the cells are substantially separated and are not overlapping in images acquired by the automated microscope.

2. The single-use cartridge of claim 1 wherein the movable valve mechanism is a rotary valve having a cylindrical stem.

3. The single-use cartridge of claim 2 wherein the metering chamber is a pass-through conduit within the cylindrical stem.

4. The single-use cartridge of claim 2 wherein the metering chamber is a recessed volume on the face of the cylindrical stem.

5. The single-use cartridge of claim 1 wherein the liquid reagent is prepackaged in a vessel on the cartridge.

6. The single-use cartridge of claim 1 wherein the liquid reagent is contained in a vessel external to the cartridge and the diluent channel is adapted to provide fluid communication between the cartridge and the external vessel.

7. The single-use cartridge of claim 1 where the liquid reagent includes a sphering agent such a zwitterionic detergent to provide isovolumetric reshaping of the red blood cells.

8. The single-use cartridge of claim 1 where the liquid reagent includes an antibody conjugated to a detectable label that targets specific cells or specific antigens associated with cells.

9. The single-use cartridge of claim 1 further comprising a photometric measuring chamber in fluid communication with the sample collection port.

10. The single-use cartridge of claim 1 wherein a portion of the imaging chamber is a photometric measuring chamber.

11. A system that includes an automated microscope for analyzing cells in a biological sample, comprising:

a single-use cartridge with a body that defines:

a) a sample collection port for receiving the sample, b) a metering chamber for holding a predetermined volume of the sample, c) a diluent channel configured to be in fluid communication with a liquid reagent, d) a mixing chamber, e) an imaging chamber adapted to allow images of the cells from the biological sample to be acquired by the automated microscope, and f) at least one movable valve mechanism configured to create fluid communication in a first position between the sample collection port and the metering chamber, and in a second position to create fluid communication between the sample contained in the metering chamber and the diluent channel, the imaging chamber and the mixing chamber;

a fluid control system comprising at least one fluid moving device and a mechanism configured to operate the at least one movable valve to sequentially (i) transfer a portion of the biological sample to fill the metering chamber, (ii) to isolate all of the volume of the biological sample contained within the metering chamber from the remaining sample, (iii) dilute the entire volume of sample contained within the metering chamber with a portion of the liquid reagent, (iv) mix the sample volume with the portion of the liquid reagent, and (v) transfer all of the mixed volume to the imaging chamber for analysis by the automated microscope.

12. The system of claim 11 wherein the portion of the liquid reagent is a pre-determined metered volume and the dimensions of the imaging chamber are pre-determined and known.

13. The system of claim 11 wherein the volume of the portion of the liquid reagent is approximate and unknown and the dimensions of the imaging chamber are approximate and unknown.

14. The system of claim 11 wherein the mixing chamber is combined with the imaging chamber such that the step of mixing the sample with the portion of the liquid reagent occurs at the same time as the step of transferring all of the mixed volume to the imaging chamber.

15. The system of claim 11 wherein the shape of the imaging chamber in planar view is serpentine.

16. The system of claim 11 wherein the total volume of the imaging chamber is less than 100 microliters and the depth is less than 200 μm.

* * * * *